US012268555B2

(12) United States Patent
Zhou et al.

(10) Patent No.: US 12,268,555 B2
(45) Date of Patent: Apr. 8, 2025

(54) FLEXIBLE SENSOR

(71) Applicant: BOE Technology Group Co., Ltd., Beijing (CN)

(72) Inventors: Tingting Zhou, Beijing (CN); Kuanjun Peng, Beijing (CN); Fangzhen Zhang, Beijing (CN); Yanan Niu, Beijing (CN); Jintao Peng, Beijing (CN); Jing Niu, Beijing (CN); Shuang Sun, Beijing (CN); Lubin Shi, Beijing (CN); Jinyu Ren, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 504 days.

(21) Appl. No.: 17/416,712

(22) PCT Filed: Sep. 28, 2020

(86) PCT No.: PCT/CN2020/118434
§ 371 (c)(1),
(2) Date: Jun. 21, 2021

(87) PCT Pub. No.: WO2022/061897
PCT Pub. Date: Mar. 31, 2022

(65) Prior Publication Data
US 2022/0354461 A1 Nov. 10, 2022

(51) Int. Cl.
*A61B 8/00* (2006.01)
*A61B 8/08* (2006.01)
(Continued)

(52) U.S. Cl.
CPC .......... *A61B 8/4494* (2013.01); *B06B 1/0207* (2013.01); *B06B 1/0622* (2013.01); *A61B 8/085* (2013.01)

(58) Field of Classification Search
CPC ......... A61B 8/4494; A61B 8/085; A61B 8/42; B06B 1/0207; B06B 1/0622; B06B 2201/76; G01L 1/16
See application file for complete search history.

(56) References Cited

U.S. PATENT DOCUMENTS

2010/0277040 A1* 11/2010 Klee .................. H10N 30/2047
29/25.35
2013/0331704 A1* 12/2013 Salzman .............. A61B 8/5223
600/459
(Continued)

FOREIGN PATENT DOCUMENTS

CN 101894855 A 11/2010
CN 106457311 A 2/2017
(Continued)

*Primary Examiner* — Yi-Shan Yang
*Assistant Examiner* — Nicholas A Robinson
(74) *Attorney, Agent, or Firm* — ArentFox Schiff LLP; Michael Fainberg

(57) ABSTRACT

Embodiments of the present disclosure provide a flexible sensor, including a flexible substrate; a plurality of ultrasonic detectors, on the flexible substrate; and a plurality of detection circuits, respectively corresponding to the ultrasonic detectors; wherein each of the detection circuits is between the flexible substrate and the corresponding ultrasonic detector, and configured to drive the ultrasonic detector to emit an ultrasonic wave, and detect a detection signal output by the ultrasonic detector after receiving the ultrasonic wave; each of the ultrasonic detectors includes: a first electrode coupled to the corresponding detection circuit, a second electrode on a side of the first electrode away from the flexible substrate, and a piezoelectric induction layer between the first electrode and the second electrode; a plurality of holes are provided in a region other than a region where the detection circuits are located.

13 Claims, 11 Drawing Sheets

(51) Int. Cl.
 *B06B 1/02* (2006.01)
 *B06B 1/06* (2006.01)

(56) References Cited

U.S. PATENT DOCUMENTS

| | | | |
|---|---|---|---|
| 2015/0345987 A1* | 12/2015 | Hajati | G01N 29/34 |
| | | | 73/661 |
| 2018/0182786 A1* | 6/2018 | Zhang | H01L 29/78678 |
| 2019/0324569 A1 | 10/2019 | Ma et al. | |

FOREIGN PATENT DOCUMENTS

| | | | | |
|---|---|---|---|---|
| CN | 106861062 A | | 6/2017 | |
| CN | 108563361 A | | 9/2018 | |
| CN | 109330623 A | * | 2/2019 | A61B 8/02 |
| CN | 111554732 A | | 8/2020 | |
| JP | 2011155573 A | | 8/2011 | |

* cited by examiner

FLEXIBLE SENSOR

The present disclosure is a National Stage of International Application No. PCT/CN2020/118434, filed on Sep. 28, 2020, which is hereby incorporated by reference in its entirety.

FIELD

The present disclosure relates to the field of detection technology, and more particularly to a flexible sensor.

BACKGROUND

With the improvement of the life levels, people are increasingly concerned with maintenance on the skin, and by detecting changes in physiological indicators of the skin of a user, a maintenance scheme can be developed for the user that conform to the characteristic of the skin. However, in the related art, the detection area of a skin detection device is small and the skin detection device cannot be fitted to the skin to perform detection.

SUMMARY

A flexible sensor provided by an embodiment of the present disclosure, includes:
  a flexible substrate;
  a plurality of ultrasonic detectors on the flexible substrate; and
  a plurality of detection circuits, respectively corresponding to the ultrasonic detectors; wherein:
  each of the detection circuits is between the flexible substrate and the corresponding ultrasonic detectors, and configured to drive the ultrasonic detectors to emit an ultrasonic wave, and detect a detection signal output by the ultrasonic detector after receiving the ultrasonic wave;
  each of the ultrasonic detectors includes: a first electrode coupled to the detection circuit, a second electrode on a side of the first electrode away from the flexible substrate, and a piezoelectric induction layer between the first electrode and the second electrode;
  a plurality of holes are provided in a region other than a region where the detection circuits are located; and the holes extend through at least a part of film layers of the detection circuits.

Optionally, in the embodiment of the present disclosure, the plurality of ultrasonic detectors share one second electrode.

Optionally, in the embodiment of the present disclosure, a supporting structure is on a side of each of at least part of the ultrasonic detectors proximate to the flexible substrate; and the ultrasonic detector extends along a first surface of the supporting structure, and the first surface are a surface of the supporting structures away from the flexible substrate.

Optionally, in the embodiment of the present disclosure, the supporting structure is a raised structure protruding towards a side of the corresponding ultrasonic detector, or the supporting structure is a recessed structure having a groove on a side away from the flexible substrate.

Optionally, in the embodiment of the present disclosure, the supporting structure is the raised structure;
  a width of the raised structure is in a range between 50 µm and 500 µm;
  a spacing between the adjacent raised structures is in a range between 100 µm and 300 µm;
  a value of the spacing between the adjacent raised structures is not equal to a value of the width of the raised structure; and
  a maximum height of the raised structure is in a range between 15 µm and 80 µm.

Optionally, in the embodiment of the present disclosure, the supporting structures are the recessed structures; and openings are formed in the grooves of the recessed structures;
  the flexible sensor further includes: a conductive connection portion between the detection circuit and the recessed structure; and
  the conductive connection portion is coupled to the first electrode through the opening, and the conductive connection portion is coupled to the detection circuit.

Optionally, in the embodiment of the present disclosure, the supporting structures are the recessed structures;
  a width of the recessed structure is in a range between 1 mm and 3 mm; and
  a depth of the groove of the recessed structure is in a range between 0.15 mm and 0.75 mm.

Optionally, in the embodiment of the present disclosure, the plurality of ultrasonic detectors are classified into a raised ultrasonic detector, a recessed ultrasonic detector, and a planar ultrasonic detector in type;
  the raised structure is on a side of the raised ultrasonic detector proximate to the flexible substrate;
  the recessed structure is on a side of the recessed ultrasonic detector proximate to the flexible substrate; and
  an orthographic projection of the planar ultrasonic detector on the flexible substrate does not overlap with an orthographic projection of the supporting structure on the flexible substrate.

Optionally, in the embodiment of the present disclosure, the plurality of the ultrasonic detectors are arranged in an array in a first direction and a second direction; and the first direction and the second direction mutually intersect; the raised ultrasonic detector, the recessed ultrasonic detector and the planar ultrasonic detector are periodically arranged in a set sequence in the first direction; and types of a row of the ultrasonic detectors in the second direction is the same.

Optionally, in the embodiment of the present disclosure, sharps and areas of the ultrasonic detectors are consistent.

Optionally, in the embodiment of the present disclosure, a detection region of the flexible sensor includes: at least one first detection region, and a second detection region in addition to the first detection region;
  the raised ultrasonic detector, the recessed ultrasonic detector and the planar ultrasonic detector are in the first detection region; and
  only the planar ultrasonic detector is in the second detection region.

Optionally, in the embodiment of the present disclosure, a detection region of the flexible sensor includes: at least one first detection region, and a second detection region in addition to the first detection region;
  the recessed ultrasonic detector and the planar ultrasonic detector are in the first detection region;
  only the planar ultrasonic detector is in the second detection region;
  the recessed structure is on the side of the recessed ultrasonic detector proximate to the flexible substrate; and
  an orthographic projection of the planar ultrasonic detector on the flexible substrate does not overlap with an orthographic projection of the supporting structure on the flexible substrate.

Optionally, in the embodiment of the present disclosure, only the recessed ultrasonic detector is in a detection region of the flexible sensor;

the recessed structure is on the side of the recessed ultrasonic detector proximate to the flexible substrate;

a width of the recessed structure is in a range between 2 mm and 6 mm; and a depth of the groove of the recessed structure is in a range between 0.5 mm and 1.5 mm.

Optionally, in the embodiment of the present disclosure, a plurality of recessed ultrasonic detectors and a plurality of raised ultrasonic detectors distributed around each of the recessed ultrasonic detectors are in a detection region of the flexible sensor;

the raised structure is on a side of each of the raised ultrasonic detectors proximate to the flexible substrate; and the recessed structure is on a side of each of the recessed ultrasonic detectors proximate to the flexible substrate.

DETAILED DESCRIPTION OF THE EMBODIMENTS

In the related art, the detection area of a skin detection device is small and the skin detection device cannot be fitted to the skin to perform detection. Based on this, an embodiment of the present disclosure provides a flexible sensor.

The detailed description of the flexible sensor provided by the embodiments of the present disclosure is described in detail below in conjunction with the accompanying drawings. The thickness and shape of various film layers in the accompanying drawings do not reflect the true scale and are intended to be illustrative of the content of the present disclosure only.

Figure 1:
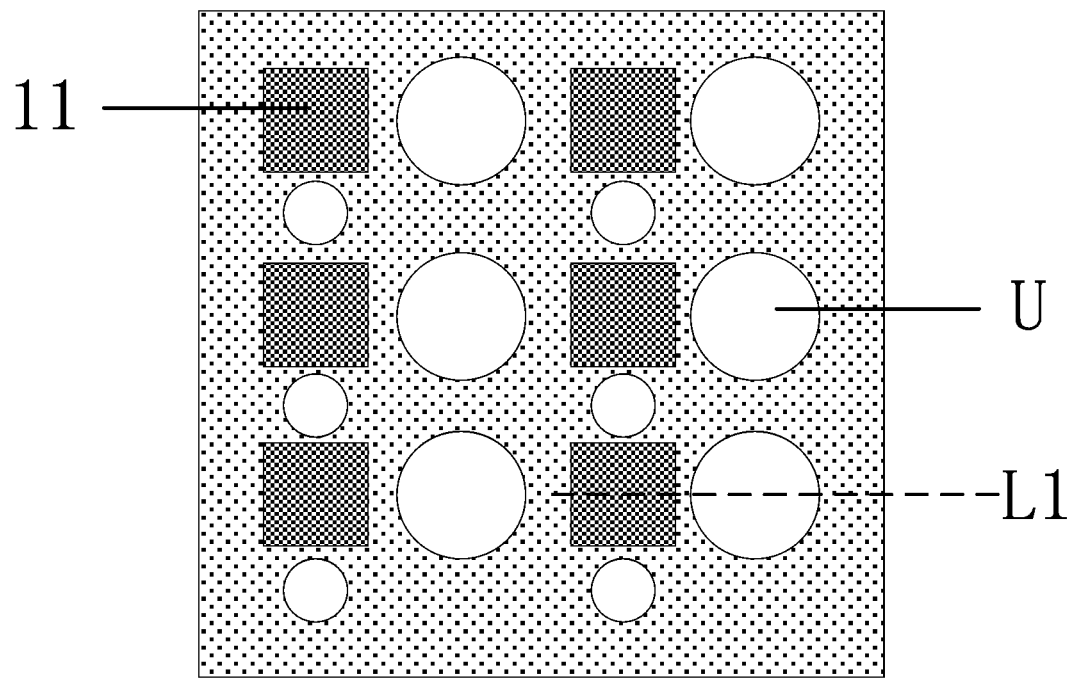
FIG. 1 is a first schematic diagram of a planar structure of a flexible sensor according to an embodiment of the present disclosure.
Figure 2:
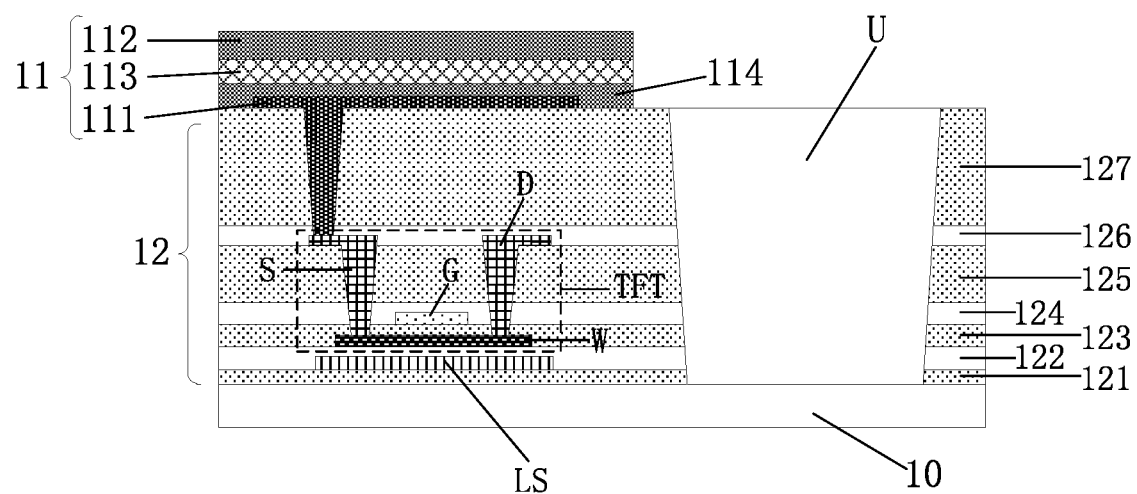
FIG. 2 is a first schematic cross-sectional diagram at a dashed line L1 in FIG. 1.

FIG. 1 is a schematic diagram of a planar structure of the flexible sensor according to the embodiment of the present disclosure, and FIG. 2 is a first schematic cross-sectional diagram at a dashed line L1 in FIG. 1. As shown in FIG. 1 and FIG. 2, the flexible sensor provided by the embodiment of the present disclosure includes:

a flexible substrate 10;

a plurality of ultrasonic detectors 11 on the flexible substrate 10; and a plurality of detection circuits 12, respectively corresponding to the ultrasonic detectors 11; wherein each of the detection circuit 12 is between the flexible substrate 10 and the corresponding ultrasonic detector 11, and configured to drive the ultrasonic detector 11 to emit an ultrasonic wave, and detect a detection signal output by the ultrasonic detector 11 after receiving the ultrasonic wave.

Each of the ultrasonic detectors 11 includes: a first electrode 111 coupled to the detection circuit 12, a second electrode 112 on a side of the first electrode 111 away from the flexible substrate 10, and a piezoelectric induction layer 113 between the first electrode 111 and the second electrode 112.

A plurality of holes U are provided in a region other than a region where the detection circuits 12 is located; and the holes U extend through at least a part of the film layers of the detection circuits 12.

According to the flexible sensor provided by the embodiments of the present disclosure, the plurality of ultrasonic detectors are disposed on the flexible substrate, so that the flexible sensor can be bent so as to be fitted to the skin to perform detection. Moreover, by providing the plurality of ultrasonic detectors on the flexible substrate, the detection area of the flexible sensor is large. In addition, by providing the plurality of holes in the region other than the region where the detection circuits 12 are located, stress may be released, and the performance of the ultrasonic detectors is prevented from being affected by the bend of the flexible sensor.

During specific implementation, the flexible substrate may be formed from polyimide, polyvinyl chloride or polyethylene, or other materials, without limitation here. By fabricating the plurality of ultrasonic detectors on the flexible substrate, the flexible sensor may be bent to be fitted to the skin when skin detection is performed, so as to improve the user's experience.

In the practical application, the area, number, arrangement, etc. of the ultrasonic detectors in the flexible sensor may be set depending on the application scenario of the flexible sensor. For example, when the flexible sensor is used to detect the forehead portion, the flexible substrate may be disposed to conform to the shape of the forehead portion, the plurality of ultrasonic detectors are disposed on the flexible substrate, and since the forehead portion is relatively flat, the ultrasonic detectors on the flexible substrate and may be uniform have the same area and may be disposed to uniform in distribution, which is exemplified only and does not limit the area, number and arrangement of the ultrasonic detectors.

Specifically, referring to FIG. 2, each of the ultrasonic detectors 11 includes: the first electrode 111, the second electrode 112 and the piezoelectric induction layer 113 between the first electrode 111 and the second electrode 112. Specifically, the piezoelectric induction layer 113 may be formed from a polyvinylidene fluoride (PVDF) material, aluminum nitride (AlN), zinc oxide (ZnO), a piezoelectric ceramic transducer (PZT) material, or other materials, and the piezoelectric induction layer 113 may also be formed using other piezoelectric materials, without limitation here. Additionally, in the embodiments of the present disclosure, a dielectric layer 114 may further be disposed between the first electrode 111 and the piezoelectric induction layer 113. By providing the dielectric layer 114, the piezoelectric induction layer 113 may be more flat, the piezoelectric induction layer 113 may have better performance and thus the ultrasonic detector 11 has the good detection effect. Due to the smaller thickness of the dielectric layer 114, an electrical signal input to the piezoelectric induction layer 113 through the first electrode 111 may not be affected.

In the embodiments of the present disclosure, the plurality of ultrasonic detectors 11 are disposed on the flexible substrate 10 and are independent from one another, moreover, at least the respective piezoelectric induction layers 113 in the respective ultrasonic detectors 11 are independent from one another. In this way, when the flexible sensor is bent, no interaction is among the respective piezoelectric induction layers 113 in the respective ultrasonic detectors 11, thereby reducing signal crosstalk among the ultrasonic detectors 11. Moreover, bending stress may be released, and the influence of bending on the piezoelectric performance of the piezoelectric induction layer 113 is reduced.

In the embodiments of the present disclosure, the corresponding detection circuits 12 are disposed between the ultrasonic detectors 11 and the flexible substrate 10. For example, the plurality of ultrasonic detectors 11 in the flexible sensor may correspond to the plurality of detection circuits 12 one to one, and other correspondence manners may also be adopted, which is not limited here. In the using process, each of the detection circuits 12 may be used to drive the corresponding ultrasonic detector 11 to emit the ultrasonic wave and to detect the detection signal output by the ultrasonic detector 11 after receiving the ultrasonic wave, so that the skin is detected. Specifically, the detection circuit 12 may include a thin film transistor TFT, the thin film transistor TFT may include an active layer W, a gate G, a source S, a drain D and other structures. Moreover, a light shading portion LS may be disposed between each the layer W and the flexible substrate 10 in order to avoid the problem that ambient light on a side of the flexible substrate 10 away from the ultrasonic detector 11 irradiates the active layer W to cause the active layer W to generate a photon-generated carrier and consequently a detection structure is affected.

In addition, as shown in FIG. 2, the flexible sensor may further include: a barrier layer 121 between the flexible substrate 10 and the light shading portion LS, a buffer layer 122 between the light shading portion LS and the active layer W, a first gate insulating layer 123 between the active layer W and the gate G, a second gate insulating layer 124 on a side of the gate G away from the flexible substrate 10, an interlayer insulating layer 125 between the second gate insulating layer 124 and the source S, a passivation layer 126 on a side of the source S away from the flexible substrate 10, and a flat layer 127 on a side of the passivation layer 126 away from the flexible substrate 10.

In the embodiments of the present disclosure, in order to avoid affecting the performance of the piezoelectric induction layers 113 in the bending process of the flexible sensor, and to reduce the influence of bending on ultrasonic wave emitting and receiving processes, the plurality of holes U are disposed in the region other than the region where the detection circuits 12 are located and extend through at least a part of the film layers of the detection circuits 12. For example, the holes U may extend through the flat layer 127 which is large in thickness, or may extend through a portion of the flat layer 127. In addition, in order to improve the stress release capacity of the holes U, the holes U may also extend through more film layers. For example, the holes U may extend through the flat layer 127 and the passivation layer 126, or may extend through all the film layers of the detection circuits 12, where the depth of the holes U is not limited here. In addition, by forming the plurality of holes U in the region other than the region where the detection circuits 12 are located, the bending curvature of the flexible sensor may be smaller, so that the flexible sensor is better fitted to the skin. Moreover, defects such as crosstalk between the adjacent ultrasonic detectors 11 may also be avoided when the flexible sensor is bent, and thus the detection accuracy is improved. During specific implementation, the shapes and sizes of the holes U may be set according to the distribution of the ultrasonic detectors 11 in the flexible sensor, where the shapes and sizes of the holes U are not limited.

During specific implementation, in order to control the respective ultrasonic detectors 11 to emit or receive the ultrasonic waves respectively, the first electrode 111 may be coupled to the source S of the thin film transistor TFT, specifically, the first electrode 111 may be coupled to the source S through a via extending through the passivation layer 126 and the flat layer 127. Furthermore, in order to provide a voltage signal to the second electrode 112, The detection circuit 12 may further include a drive signal line (not shown) coupled to the second electrode 112, and a plurality of read signal lines (not shown) coupled to the drains D of the thin film transistors TFT respectively.

During an ultrasonic wave emitting stage, a fixed voltage signal may be input to the first electrode 111, for example, the fixed voltage signal may be 0 V. During specific implementation, all thin film transistors TFT may be controlled to turn on and the fixed voltage signal is applied to the drain D of each of the thin film transistor TFT so as to apply the fixed voltage signal to each of the first electrode 111. A drive signal is input to the second electrode 112, for example, a high voltage alternating current signal is input, which may be about 100 V, and an emitting frequency of which is in the range of 5 to 15 MHz. Specifically, the drive signal line may be used for applying a drive signal to the second electrode 112, thereby driving the piezoelectric material in the piezoelectric induction layer 113 to deform or vibrate, so as to generate the ultrasonic wave.

Figure 3:
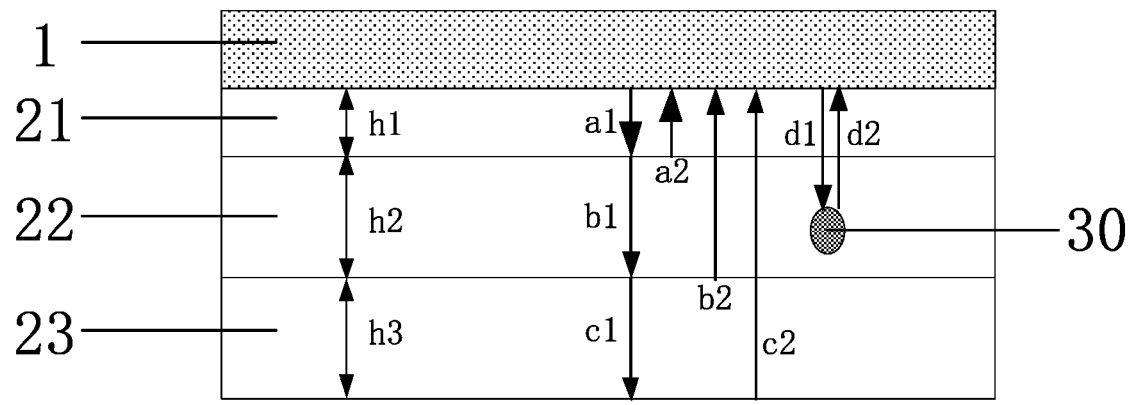
FIG. 3 is a schematic diagram of skin detection by a flexible sensor.

FIG. 3 is a schematic diagram of skin detection by the flexible sensor. As shown in FIG. 3, skin generally may include epidermis 21 and dermis 22. A thickness h1 of the epidermis 21 is about 0.04 mm to 0.1 mm, and a thickness h2 of the dermis 22 is about 0.6 mm to 2 mm. Subcutaneous tissue 23 is on a side of the dermis 22 away from the epidermis 21, and a thickness h3 of the subcutaneous tissue 23 is about 3 mm to 10 mm. In the detection process, the flexible sensor 1 is attached to the surface of the skin, the ultrasonic wave generated by the flexible sensor 1 can propagate in the skin, and moreover, the ultrasonic wave will be reflected at an interface between the epidermis 21, the dermis 22, an interface between the dermis 22 and the subcutaneous tissue 23 as well as a location of an abnormal defect 30 in the skin. Referring to FIG. 3, when an ultrasonic wave a1 propagates to an interface between the epidermis 21 and the dermis 22, a part of the ultrasonic wave is reflected to obtain an ultrasonic wave a2, and the other part of the ultrasonic wave continues to propagate to obtain an ultrasonic wave b1. The ultrasonic wave b1 propagates to an interface between the dermis 22 and the subcutaneous tissue 23, a part of the ultrasonic wave b1 is reflected to obtain an ultrasonic wave b2, and the other part of the ultrasonic wave b1 continues to propagate to obtain an ultrasonic wave c1. The ultrasonic wave c1 is reflected at the lower surface of the subcutaneous tissue 23 to obtain an ultrasonic wave c2, an ultrasonic wave d1 irradiates the location of the defect 30 to be reflected to obtain an ultrasonic wave d2, and the ultrasonic sensor 1 receives the reflected ultrasonic waves a2, b2, c2 and d2. According to echo intensity and receiving time, the type and location of the defect 30 may be determined.

During an ultrasonic wave receiving stage, referring to FIGS. 2 and 3 simultaneously, a fixed voltage signal is input to the second electrode 112, for example, the fixed voltage signal may be 0 V. Specifically, the drive signal line may be used for applying the fixed voltage signal to the second electrode 112. After the flexible sensor 1 receives the reflected ultrasonic wave, the piezoelectric induction layer 113 receives the ultrasonic wave and convert it into an electric current, a detection current is received through the first electrode 111, and then through the thin film transistor TFT and an amplification circuit (not shown), a magnitude of the detection current is obtained. For example, a manner of turning on the thin film transistors TFT row by row may be adopted, the detection current received by the respective first electrodes 111 is obtained through the respective read signal lines, and then the obtained detection current is amplified through an amplifying current to obtain the intensity of the ultrasonic wave received by the ultrasonic detector 11, and therefore the type and location of the defect 30 are determined.

Figure 4:
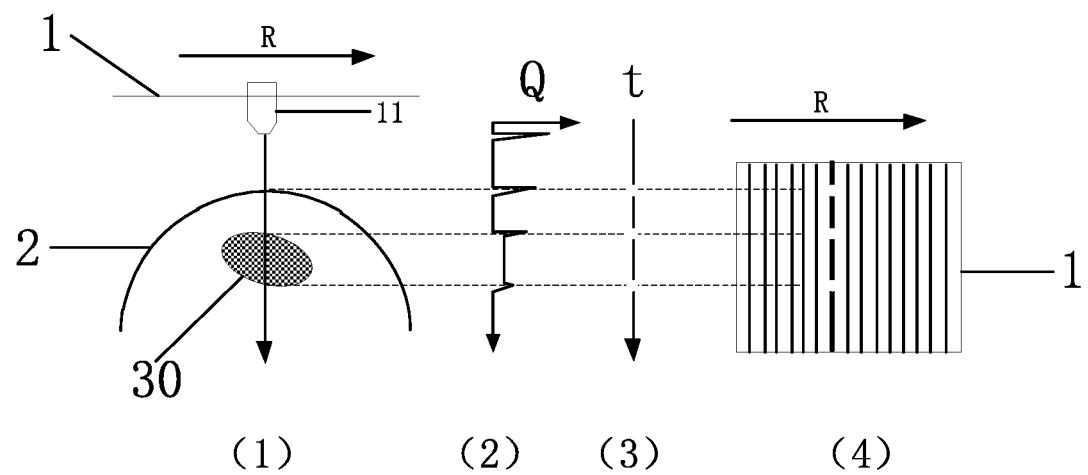
FIG. 4 is a schematic diagram of a flexible sensor in a scanning process.

In the practical application, in order to obtain the detection currents output by the ultrasonic detectors 11 respectively, each ultrasonic detector 11 may be controlled to output the detection current in scanning and time-sharing manners. FIG. 4 is a schematic diagram of the flexible sensor in a scanning process. As shown in FIG. 4, a part (1) in the figure indicates that an ultrasonic wave emitted by a certain ultrasonic detector 11 is directed at the surface of the skin 2, propagates in the skin 2 and is directed at the defect 30. A part (2) in the figure represents an echo intensity curve, and the location of a peak in the echo intensity curve represents that the ultrasonic wave propagates to the location of the interface. A part (3) in the figure represents the time at which the ultrasonic wave propagates to the location of the interface, and with the echo intensity curve and the time at which the ultrasonic wave propagates to the location of the interface, a specific location of the defect 30 may be obtained. A part (4) in the figure indicates that the flexible sensor 1 scans in a direction indicated by an arrow R, stripes in the flexible sensor 1 represent emitting positions of the ultrasonic detector, and the horizontal position of the defect 30 may be obtained by time-sharing detection in the manner of scanning, so that the specific position of the defect 30 in the skin may be accurately determined.

Moreover, a proper ultrasonic wave can have a noticeable softening and dispersing effect on a scar, can promote softening of tissue damage fibers and tissue, and ultimately achieves the scar removal. Besides, the proper ultrasonic wave may increase the permeability of a skin blood vessel to make the skin slightly hyperemic without erythema, and may also enhance skin sweat gland secretion to promote skin excretion and enhance skin regenerative capacity, and as such, the skin may be repaired with the flexible sensor provided by the embodiments of the present disclosure.

Figure 5:
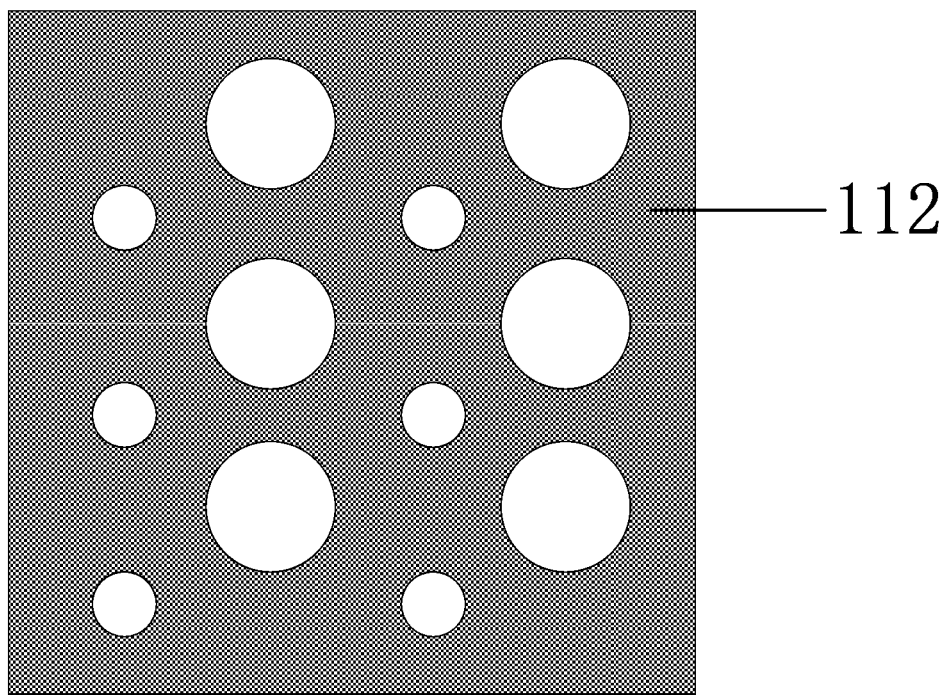
FIG. 5 is a schematic structural diagram of a second electrode shared by a plurality of ultrasonic detectors in the embodiment of the present disclosure.

Optionally, in the flexible sensor provided by the embodiments of the present disclosure, as shown in FIG. 5, the plurality of ultrasonic detectors share one second electrode 112.

Since the respective signals input to the second electrode in the respective ultrasonic detectors in the detection process are the same, the ultrasonic detectors can share one second electrode 112, which may reduce the number of the signal lines, save the fabrication cost, and facilitate driving each ultrasonic detector. With simultaneous reference to FIG. 1, since the holes U are further formed in the region other than the region where the detection circuits 12 are located, when the depth of the holes U is great, during fabrication, the second electrode 112 may be disconnected at edges of the holes U, and thus, in FIG. 5, the second electrode 112 has through holes corresponding to the holes U. During specific implementation, when the depth of the holes U is small, the second electrode 112 may not be disconnected at the edges of the holes U, i.e., the second electrode 112 may also be a full surface structure without through holes.

In addition, each second electrode may also be disposed to correspond to one first electrode, alternatively, all the first electrodes may also be disposed to correspond to at least two second electrodes, and the correspondence relationship between the first electrodes and the second electrodes is not limited here.

Figure 6:
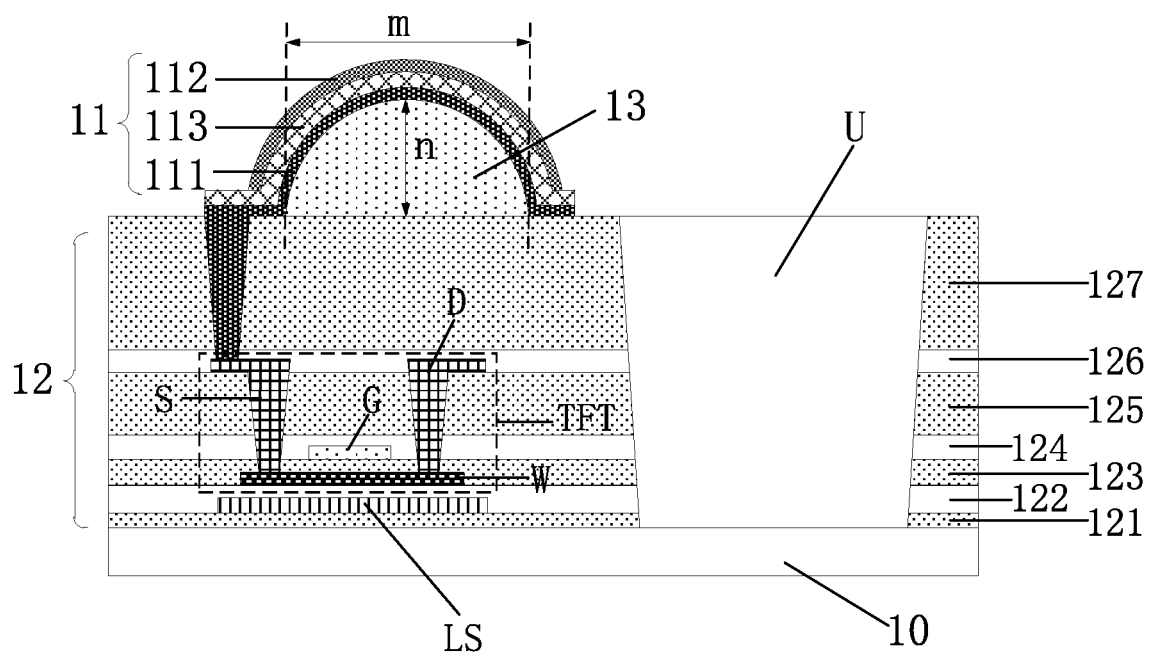
FIG. 6 is second schematic cross-sectional diagram at the dashed line L1 in FIG. 1.
Figure 7:
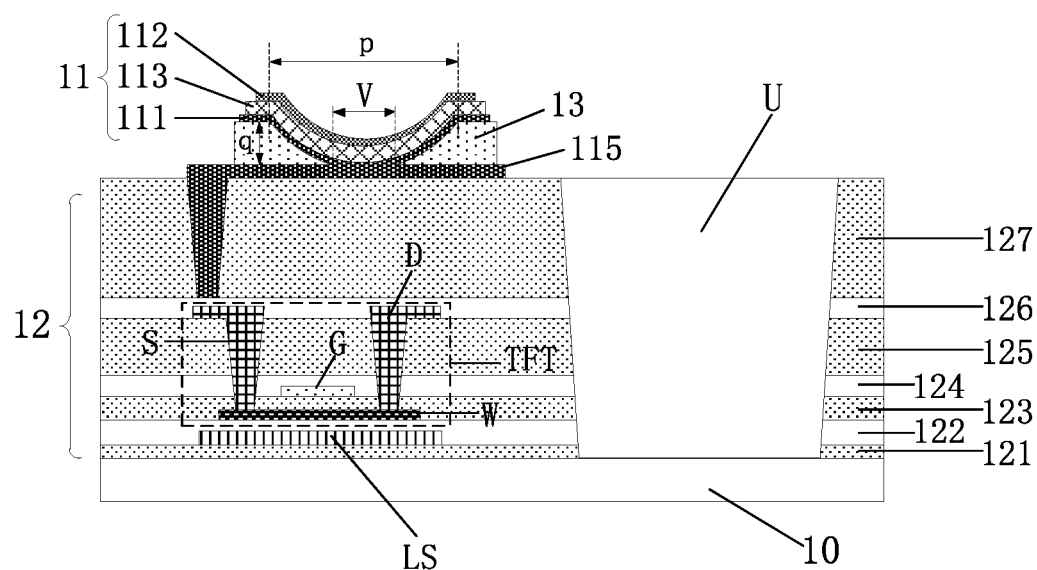
FIG. 7 is a third schematic cross-sectional diagram at the dashed line L1 in FIG. 1.

Further, in the flexible sensor provided by the embodiments of the present disclosure, FIG. 6 is a second schematic cross-sectional diagram at the dashed line L1 in FIG. 1, FIG. 7 is a third schematic cross-sectional diagram at the dashed line L1 in FIG. 1, and as shown in FIG. 6 and FIG. 7, a supporting structure 13 is disposed on a side of at least part of the ultrasonic detectors 11 proximate to the flexible substrate 10.

The ultrasonic detector 11 extends along a first surface of the supporting structure 13, and the first surface is a surface of the supporting structure 13 away from the flexible substrate 10, i.e., the first surface is an upper surface of the supporting structure 13 in the figures.

In the embodiments of the present disclosure, the supporting structure 13 is provided on the side of the ultrasonic detector 11 proximate to the flexible substrate 10, so that the ultrasonic detector 11 may be supported, thereby further reducing the influence on the piezoelectric induction layer 113 in the bending process of the flexible sensor. Moreover, the ultrasonic detector 11 extends along the first surface of the supporting structure 13, and ultrasonic wave diverging and focusing may be achieved by setting the shape of the supporting structure 13. During specific implementation, the supporting structure 13 may be provided under part of the ultrasonic detectors 11 in the flexible sensor, the supporting structure 13 may also be provided under each of the ultrasonic detectors 11, and the supporting structure may be disposed according to an application scenario of the flexible sensor, which is not limited here.

Specifically, in the flexible sensor provided by the embodiments of the present disclosure, the supporting structure may be one of following structures.

Structure 1: as shown in FIG. 6, the supporting structure 13 is a raised structure protruding towards a side of the corresponding ultrasonic detector 11, and the ultrasonic detector 11 extends along the upper surface of the supporting structure 13, so that the ultrasonic detector 11 is also raised, and the ultrasonic wave emitted by the ultrasonic detector 11 is relatively diverged.

Structure 2: as shown in FIG. 7, the supporting structure 13 is a recessed structure having a groove on a side away from the flexible substrate 10, and the ultrasonic detector 11 extends along the upper surface of the supporting structure 13, so that the ultrasonic detector 11 is also recessed, and the ultrasonic wave emitted by the ultrasonic detector 11 is relatively converged.

As shown in FIG. 6, the supporting structure 13 is the raised structure. During a fabrication process, all film layers of the detection circuit 12 are formed on the flexible substrate 10. Moreover, a hole U may be formed in the patterning process of the film layers of the detection circuit 12, and then the raised structure is formed from an organic material on the detection circuit 12. Specifically, the raised structure may be fabricated by nano-imprinting or by etching. By providing the hole U and the raised structure, the influence on the piezoelectric induction layer 113 may be effectively reduced when the flexible sensor is bent. After that, the first electrode 111 is fabricated on the raised structure and is coupled to the thin film transistor TFT, a piezoelectric induction thin film is formed on the first electrode 111 and subjected to patterning so as to obtain the piezoelectric induction layer 113 in each ultrasonic detector 11. In this way, signal crosstalk among the ultrasonic detectors 11 can be reduced, bending stress may be released, and the influence of bending on piezoelectric performance of the piezoelectric induction layer 113 is reduced. The second electrode 112 is formed after the piezoelectric induction layer 113 is formed.

In addition, to facilitate coupling between the thin film transistor TFT in the detection circuit 12 and the first electrode 111, the position of the raised structure may be set by avoiding a through hole connected with the first electrode 111 in the flat layer 127.

In the embodiments of the present disclosure, in order to avoid the influence on the performance of the piezoelectric induction layer when the flexible sensor is bent, the plurality of discrete ultrasonic detectors are disposed on the flexible substrate, and the plurality of holes are formed in the region other than the region where the detection circuits are located. However, compared with whole-surface arrangement of the piezoelectric induction layer of the flexible sensor, the effective area of the piezoelectric induction layer in the flexible sensor in the embodiments of the present disclosure is lowered, and in the detection process, the uniformity of the ultrasonic wave received by the skin is poor. By providing the raised structure on the side of the ultrasonic detector proximate to the flexible substrate, the ultrasonic detector may also be raised, and thus the ultrasonic wave emitted by the ultrasonic detector is diverged, the uniformity of the ultrasonic wave received by the skin is good, and the ultrasonic wave propagating in the skin also evenly covers the skin. The situation that the defect in the skin cannot be detected due to the poor uniformity of the ultrasonic wave is avoided, and thus detection accuracy is improved. In addition, when the above supporting structure is the raised structure, the raised ultrasonic detector may be controlled to emit the ultrasonic wave with the weak intensity and good uniformity to the skin so as to increase the permeability of the skin blood vessel to make the skin slightly hyperemic but without erythema, and skin sweat gland secretion may be enhanced to promote a skin excretion function and improve skin regenerative capacity.

Specifically, in the flexible sensor provided by the embodiments of the present disclosure, as shown in FIG. 6, the supporting structure 13 is the raised structure.

A width m of the raised structure is in a range between 50 μm and 500 μm. The width m of the raised structure is set to be greater than 50 μm, so that the requirement for a fabrication process is low, and the raised structure with good morphology can be easily formed. The width m of the raised structure is set to be lower than 500 μm, so that it may be guaranteed that the uniformity of the ultrasonic wave formed by the flexible sensor is good. A spacing (not shown) between the adjacent raised structures is in a range between 100 μm and 300 μm. The spacing between the adjacent raised structures is set to be greater than 100 so that it may be guaranteed that when the flexible sensor is bent, the adjacent ultrasonic detectors 11 will not extrude each other so as to avoid mutual influence between them. The spacing between the adjacent raised structures is set to be lower than 300 μm, so that it may be guaranteed that the uniformity of the ultrasonic wave formed by the flexible sensor is good. It is avoided that since the adjacent raised structures are distantly spaced, the ultrasonic wave between the adjacent raised structures is weak, and consequently the uniformity of the ultrasonic wave formed by the flexible sensor is poor. A value of the spacing between the adjacent raised structures is not equal to a value of the width m of the raised structure, so that mutual interference of the ultrasonic waves emitted by the adjacent ultrasonic detectors 11 is avoided. For example, when a ratio of the width m of the raised structure to the spacing between the adjacent raised structures is 1:2, the uniformity of the ultrasonic wave formed by the flexible sensor is good. The maximum height n of the raised structure is in a range between 15 μm and 80 μm. The maximum height n of the raised structure is set to be greater than 15 μm, so that it may be guaranteed that the raised structure can support the corresponding ultrasonic detector 11, and the corresponding ultrasonic detector 11 is made to also have the raised structure. The maximum height n of the raised structure is set to be lower than 80 μm, so that the divergence effect of the ultrasonic wave generated by the ultrasonic detector 11 is good, and it is guaranteed that the divergence effect of the ultrasonic wave formed by the flexible sensor is good.

In the practical application, the width and maximum height of the raised structure are related to the effective area of the piezoelectric induction layer, the ultrasonic wave emitting frequency, the application scenario of the flexible sensor and other factors. Parameters, such as the width and maximum height, of the raised structure are analyzed in detail below in conjunction with a simulation experiment, and the following analysis takes the ultrasonic wave emitting frequency of the flexible sensor being 5 MHz as an example.

Firstly, comparative examples one, two and three are compared. A piezoelectric induction layer of the flexible sensor in comparative example one is a whole-surface, and no supporting structure is provided in the flexible sensor. The flexible sensor in comparative example two has a plurality of discrete piezoelectric induction layers, but the flexible sensor is not provided with a supporting structure. The flexible sensor in comparative example three has the raised structure therein, the raised structure has the width of about 100 μm and the maximum height of about 25 μm, and the spacing between the adjacent raised structures is about 200 μm. The other structures in comparative examples one, two and three are the same. From simulated analysis, it is known that the total acoustic field of the ultrasonic wave emitted by the flexible sensor in comparative example one is uniform in distribution; the uniformity of the total acoustic field of the ultrasonic wave emitted by the flexible sensor in comparative example two is poor; and the uniformity of the total acoustic field of the ultrasonic wave emitted by the flexible sensor in comparative example three is good. Therefore, it may be demonstrated that by providing the raised structure, the uniformity of the ultrasonic wave emitted by the flexible sensor can be improved.

After that, the reference to the raised structure is analyzed through a simulation experiment.

When the width of the raised structure is 100 μm and the spacing between the adjacent raised structures is 200 μm, and maximum heights of comparative raised structures are respectively 15 μm, 20 μm, 25 μm, 30 μm, 35 μm, 40 μm and 50 μm, as for the uniformity of ultrasonic waves of flexible sensors, it can be known through simulated analysis that the uniformity of the total acoustic field of the ultrasonic wave emitted by the flexible sensor with the maximum height of the raised structure being 25 μm is good.

When the width of the raised structure is 50 μm and the spacing between the adjacent raised structures is 100 μm, and the maximum heights of the comparative raised structures are respectively 15 μm, 20 μm and 25 μm, as for the uniformity of the ultrasonic waves of the flexible sensors, it can be known through simulated analysis that the uniformity of the total acoustic field of the ultrasonic wave emitted by the flexible sensor with the maximum height of the raised structure being in a range between 20 μm and 25 μm is good.

When the width of the raised structure is 500 μm and the spacing between the adjacent raised structures is 500 μm, and the maximum heights of the comparative raised structures are respectively 50 μm, 60 μm, 75 μm, 80 μm, 100 μm and 150 μm, as for the uniformity of ultrasonic waves of the flexible sensors, it can be known through simulated analysis that the uniformity of the total acoustic field of the ultrasonic wave emitted by the flexible sensor is poor due to the fact that the spacing between the adjacent raised structures is large.

When the width of the raised structures is 500 μm and the spacing between the adjacent raised structures is 300 μm, and the maximum heights of the comparative raised structures are respectively 50 μm, 60 μm and 75 μm as for the uniformity of the ultrasonic waves of the flexible sensors, it can be known through simulated analysis that the uniformity of the total acoustic field of the ultrasonic wave emitted by the flexible sensor with the maximum height of the raised structure being 60 μm is good.

When the width of the raised structures is 500 μm and the spacing between the adjacent raised structures is 200 μm, and the maximum heights of the comparative raised structures are respectively 50 μm, 60 μm, 70 μm, 75 μm, 80 μm and 100 μm, as for the uniformity of the ultrasonic waves of the flexible sensors, it can be known through simulated analysis that the uniformity of the total acoustic field of the ultrasonic wave emitted by the flexible sensor with the maximum height of the raised structure being in a range between 70 μm and 80 μm is good. Besides, through comparison to the total acoustic field of the ultrasonic waves when the width of the raised structure is 500 μm and the spacing between the adjacent raised structures is 300 μm, it can be known that the uniformity of the ultrasonic wave can be improved by reducing the spacing between the adjacent raised structures.

As shown in FIG. 7, the supporting structure 13 is the recessed structure; and an opening V is formed in the groove of the recessed structure.

The flexible sensor may further include: a conductive connection portion 115 between the detection circuit 12 and the recessed structure.

The conductive connection portion 115 is coupled to the first electrode 111 through the opening V, and the conductive connection portion 115 is coupled to the detection circuit 12.

Since the groove are formed in the side of the recessed structure away from the flexible substrate 10, a segment difference at an edge position of the recessed structure is large. If the first electrode 111 is disposed to extend down from edges of the recessed structure to be coupled to the detection circuit 12, during a fabrication process, the first electrode 111 is possibly broken at the edges of the recessed structure, and thus connection performance between the first electrode 111 and the detection circuit 12 is affected. Therefore, in the embodiments of the present disclosure, by forming the opening V in the groove of the recessed structure, the first electrode 111 is coupled to the conductive connection portion 115 through the opening V, and the first electrode is coupled to the detection circuit 12 through the conductive connection portion 115, so that it is guaranteed that the connection performance between the first electrode 111 and the detection circuit 12 is good. Forming the opening V in the groove of the recessed structure will not affect the overall shape of the recessed structure, so that the performance of the ultrasonic detector will not be affected.

Referring to FIG. 7, during the fabrication process, the film layers of the detection circuit 12 are formed on the flexible substrate 10, a hole U may be formed during patterning of the film layers of the detection circuit 12, then the conductive connection portion 115 is formed on the detection circuit 12, and the recessed structure is formed from an organic material on the film layer 12 where the conductive connection portion 115 is located. Specifically, the recessed structure may be fabricated by nano-imprinting or by etching. By providing the hole U and the recessed structure, the influence on the piezoelectric induction layer 113 may be effectively reduced when the flexible sensor is bent. After that, the first electrode 111 is fabricated on the recessed structure and is coupled to the thin film transistor TFT, a piezoelectric induction thin film is formed on the first electrode 111 and subjected to patterning so as to obtain the piezoelectric induction layer 113 in each ultrasonic detector 11. In this way, signal crosstalk among the ultrasonic detectors 11 can be reduced, bending stress may be released, and the influence of bending on piezoelectric performance of the piezoelectric induction layers 113 is reduced. The second electrode 112 is formed after the piezoelectric induction layer 113 is formed.

In addition, to facilitate coupling between the thin film transistor TFT in the detection circuit 12 and the first electrode 111, the position of the recessed structure may be set by avoiding a through hole connected with the first electrode 111 in the flat layer 127.

Specifically, in the flexible sensor provided by the embodiments of the present disclosure, as shown in FIG. 7, the supporting structure 13 is the recessed structure.

A width p of the recessed structure is in a range between 1 mm and 3 mm. The width p of the recessed structure is set to be greater than 1 mm, so that the requirement for a fabrication process is low, and the recessed structure with good morphology can be easily formed. The width p of the recessed structure is set to be lower than 3 mm, so that it may be guaranteed that the focusing effect of the ultrasonic wave emitted by the ultrasonic detector 11 on the recessed structure is good. In order to make the focusing effect of the ultrasonic wave of the ultrasonic detector 11 on the recessed structure good, the width p of the recessed structure may be set between 1 mm and 2 mm. A depth q of the groove of the recessed structure is in a range between 0.15 mm and 0.75 mm. The depth q of the groove of the recessed structure is set to be greater than 0.15 mm, so that it may be avoided that the focusing effect of the ultrasonic wave emitted by the ultrasonic detector on the recessed structure is poor due to the too shallow groove of the recessed structure. The depth q of the groove of the recessed structure is set to be lower than 0.75 mm, it may be avoided that the ultrasonic wave emitted by the ultrasonic detector on the recessed structure is excessively focused due to the too deep groove of the recessed structure, and consequently the uniformity of the ultrasonic wave is poor. In order to make the focusing effect of the ultrasonic wave emitted by the ultrasonic detector on the recessed structure good, the depth of the groove of the recessed structure may be set between 0.15 mm and 0.5 mm.

In the practical application, the width p of the recessed structure and the depth q of the groove are related to the ultrasonic wave emitting frequency, the application scenario of the ultrasonic detector and other factors. Parameters, such as the width of the recessed structure and the depth of the groove, of the recessed structure are analyzed in detail below in conjunction with a simulation experiment.

Figure 8:
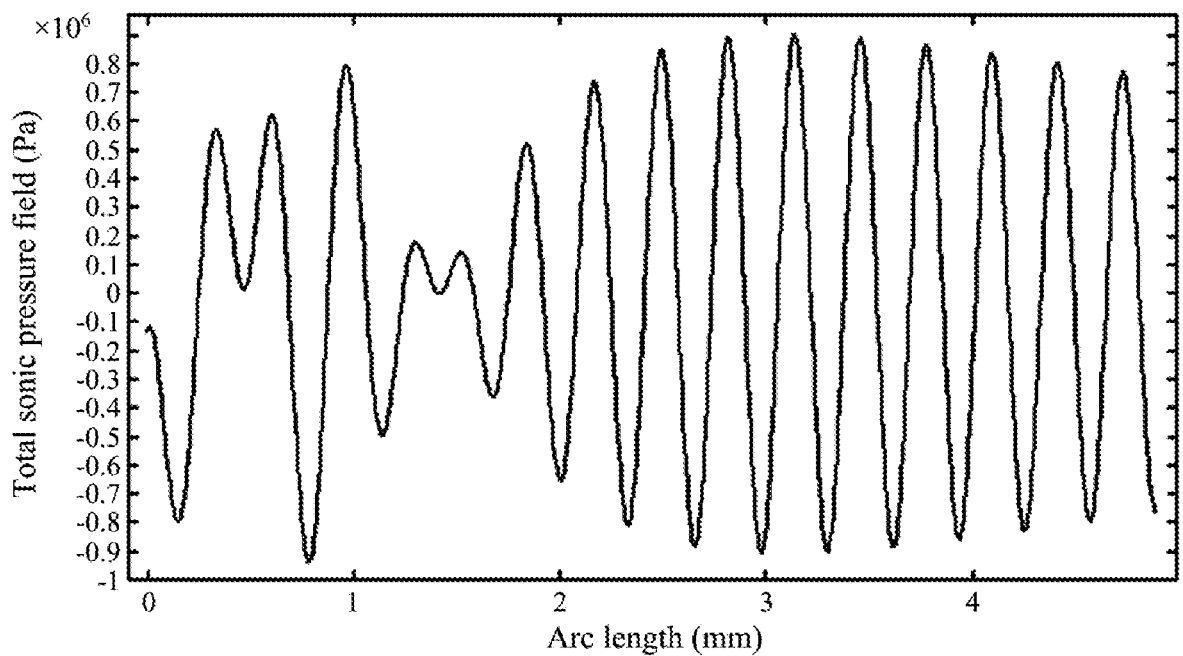
FIG. 8 is a schematic diagram of change of a total acoustic field with a detection depth of an ultrasonic detector without a supporting structure.
Figure 9:
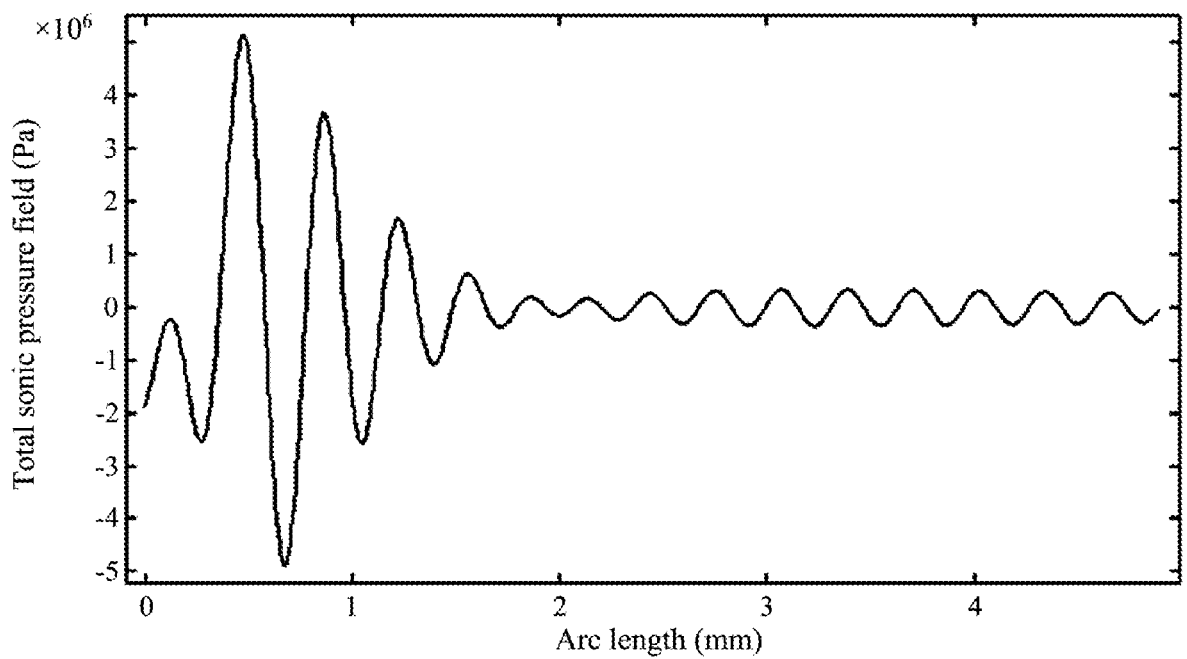
FIG. 9 is a schematic diagram of change of a total acoustic field with a detection depth of an ultrasonic detector provided with a recessed structure.

FIG. 8 is a schematic diagram of change of a total acoustic field with a detection depth of an ultrasonic detector without a supporting structure. FIG. 9 is a schematic diagram of change of a total acoustic field with a detection depth of an ultrasonic detector provided with the recessed structure. The width of the recessed structure in FIG. 9 is about 2 mm, and the depth of the groove is about 0.5 mm. In the figure, the abscissa (arc length) represents the detection depth, and the ordinate represents a total sonic pressure field of ultrasonic wave emitted by the ultrasonic detector. It can be known from FIG. 8 that with the change of the detection depth, the total sonic pressure field of the ultrasonic wave emitted by the ultrasonic detector is relatively uniform in distribution, but is relatively low in intensity, about 0.8e6 Pa. It can be known from FIG. 9 that by providing the recessed structure, the ultrasonic wave emitted by the ultrasonic detector may be focused. In FIG. 9, the ultrasonic wave is focused in a range between 0.5 mm and 1 mm, and the ultrasonic wave has relatively high total sonic pressure field intensity within the range, about 5e6 Pa. It can be known by comparing FIG. 8 and FIG. 9 that by providing the recessed structure, the total sonic pressure field intensity of the ultrasonic wave may be greatly improved by at least 6 times, so that the detection accuracy of the ultrasonic detector is improved. Therefore, the ultrasonic detector with the recessed structure may be configured to mainly measure the defect in the dermis, e.g., measuring breaking and deletion of collagen, and additionally, the ultrasonic detector may also be used for skin repairing.

Figure 10:
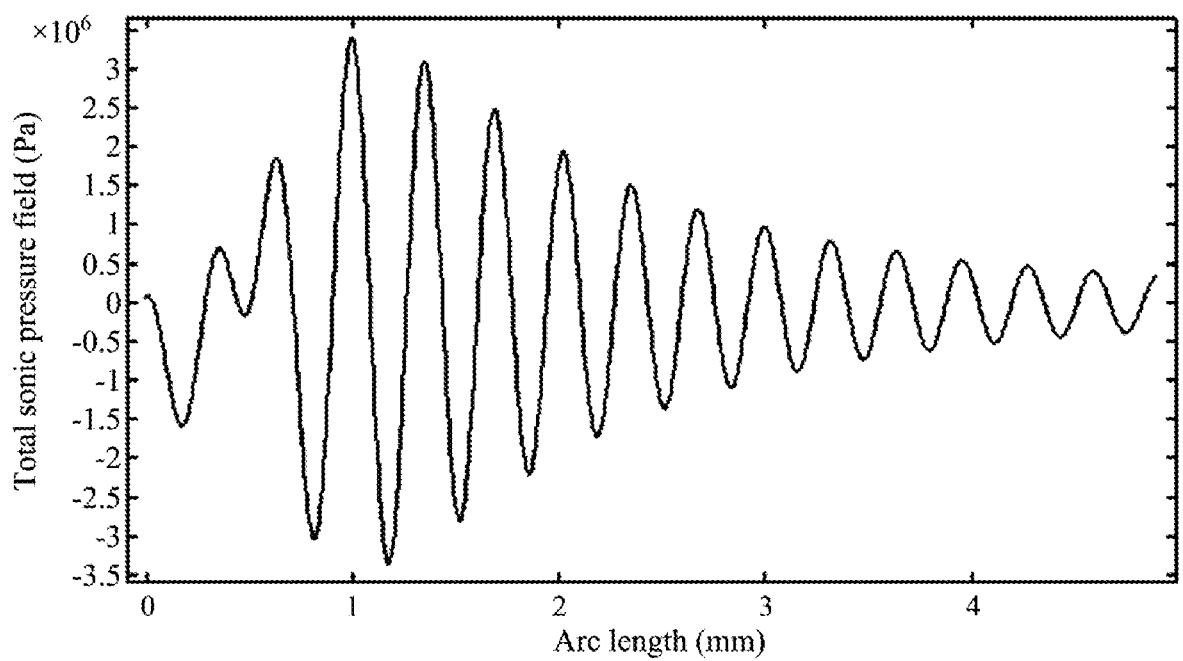
FIG. 10 is a schematic diagram of change of a total acoustic field with a detection depth of a corresponding ultrasonic detector when a groove of a recessed structure has a depth of 0.3 mm and a width of the recessed structure is 2 mm.

FIG. 10 is a schematic diagram of change of a total acoustic field with a detection depth of a corresponding ultrasonic detector when a groove of a recessed structure has a depth of 0.3 mm and a width of the recessed structure is 2 mm. In the figure, the abscissa (arc length) represents the detection depth, and the ordinate represents a total sonic pressure field of the ultrasonic wave emitted by the ultrasonic detector. It can be known from FIG. 10 that the ultrasonic wave emitted by the ultrasonic detector is focused in a range between 1 mm and 2 mm, the total sonic pressure field intensity of the ultrasonic wave within the range may reach 3.5e6 Pa, and the ultrasonic detector may be configured to detect a deep position in the dermis of the skin.

Figure 11:
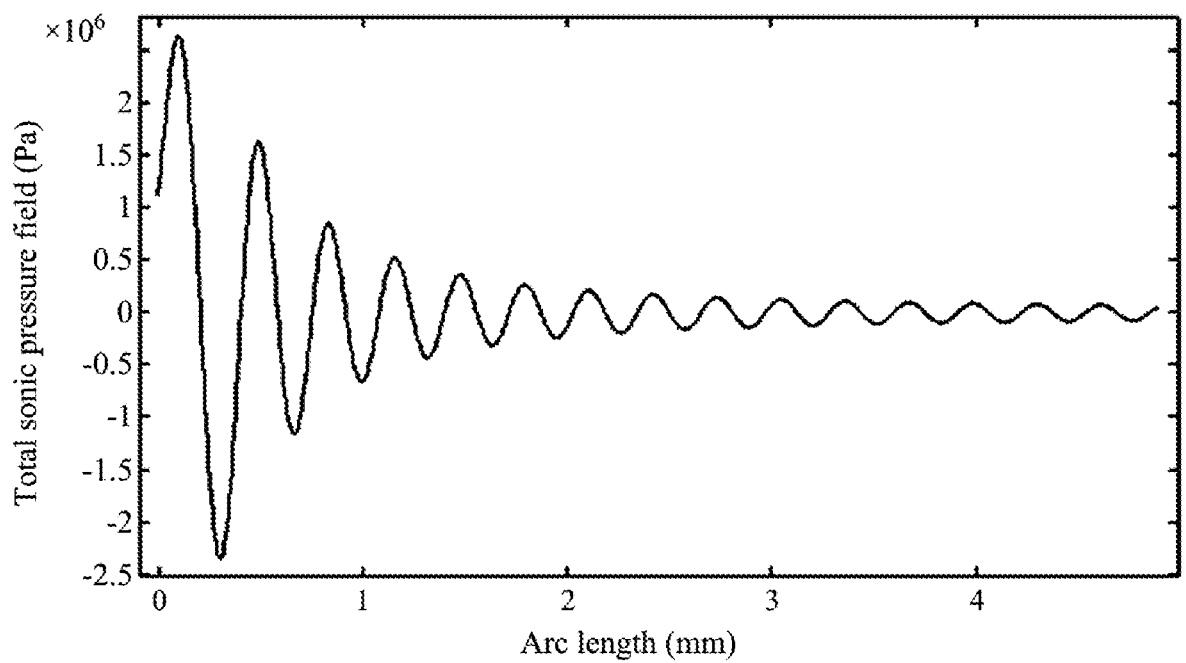
FIG. 11 is a schematic diagram of change of a total acoustic field with a detection depth of a corresponding ultrasonic detector when a groove of a recessed structure has a depth of 0.25 mm and a width of the recessed structure is 1 mm.

FIG. 11 is a schematic diagram of change of a total acoustic field with a detection depth of a corresponding ultrasonic detector when a groove of a recessed structure has a depth of 0.25 mm and a width of the recessed structure is 1 mm. In the figure, the abscissa (arc length) represents the detection depth, and the ordinate represents a total sonic pressure field of the ultrasonic wave emitted by the ultrasonic detector. It can be known from FIG. 11 that the ultrasonic wave emitted by the ultrasonic detector is focused in a range between 0.1 mm and 0.2 mm, and the ultrasonic detector may be configured to detect a position in the epidermis of the skin. It can be known by comparing FIG. 10 and FIG. 11 that the focusing depth of the corresponding ultrasonic detector is lowered after the width of the recessed structure and the depth of the groove are reduced.

Figure 12:
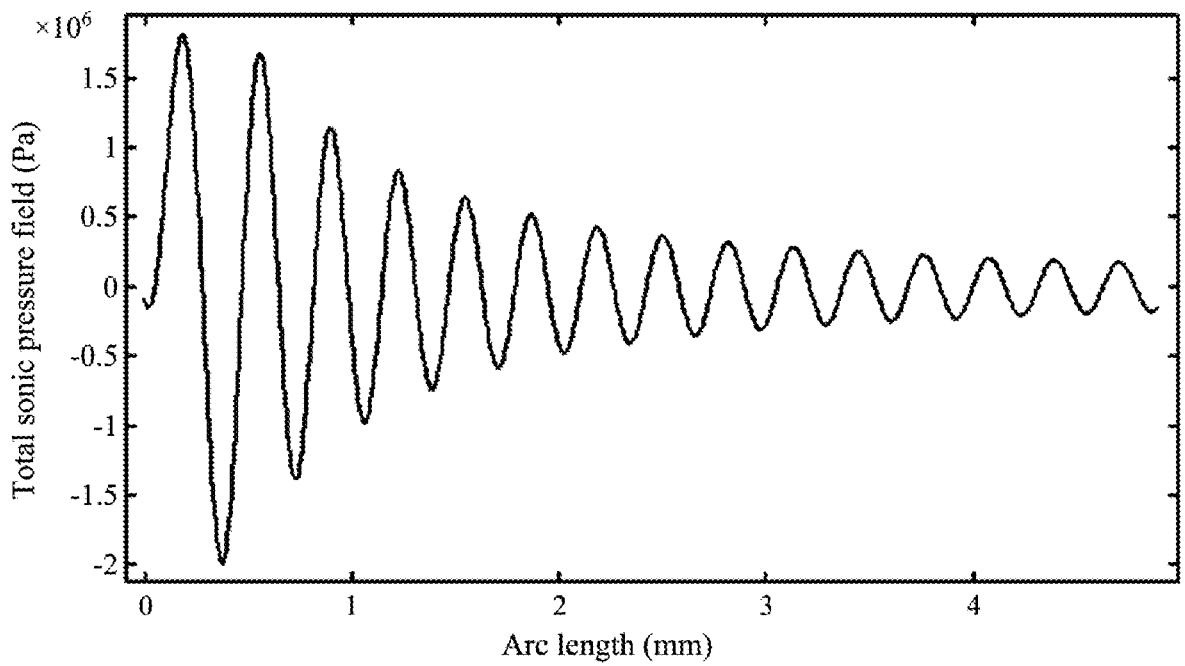
FIG. 12 is a schematic diagram of change of a total acoustic field with a detection depth of a corresponding ultrasonic detector when a groove of a recessed structure has a depth of 0.15 mm and a width of the recessed structure is 1 mm.

FIG. 12 is a schematic diagram of change of a total acoustic field with a detection depth of a corresponding ultrasonic detector when a groove of a recessed structure has a depth of 0.15 mm and a width of the recessed structure is 1 mm. In the figure, the abscissa (arc length) represents the detection depth, and the ordinate represents a total sonic pressure field of the ultrasonic wave emitted by the ultrasonic detector. It can be known from FIG. 12 that the ultrasonic wave emitted by the ultrasonic detector is focused in a range between 0.2 mm and 0.6 mm, and the ultrasonic detector may be configured to detect a position in the epidermis of the skin. It can be known by comparing FIG. 10 and FIG. 12 that the focusing depth of the corresponding ultrasonic detector is lowered after the width of the recessed structure and the depth of the groove are reduced.

To sum up, referring to FIG. 7, by providing the recessed structure on the side of the ultrasonic detector 11 proximate to the flexible substrate 10, the focusing effect of the ultrasonic wave emitted by the corresponding ultrasonic detector 11 can be made better, and the ultrasonic detector can be used to focus on the detection of the defect at a certain depth in the skin. Moreover, the intensity of the ultrasonic wave with the good focusing effect is larger and the echo signal to noise is relatively high, so that detection results are more accurate. Furthermore, since the total acoustic field intensity of the ultrasonic wave emitted by the ultrasonic detector on the recessed structure is large, the ultrasonic wave can be focused at a certain depth in the skin for targeted skin repairing. For example, a certain amount of the ultrasonic wave may have a pronounced softening effect on scars, thereby promoting softening of tissue damage fibers, and eventually reaching the effect of scar removal.

In an implementation, in the flexible sensor provided by the embodiments of the present disclosure, the plurality of ultrasonic detectors are classified into the raised ultrasonic detector, the recessed ultrasonic detector, and the planar ultrasonic detector in type.

The raised structure is provided on the side of the raised ultrasonic detector proximate to the flexible substrate.

The recessed structure is provided on the side of the recessed ultrasonic detector proximate to the flexible substrate.

An orthographic projection of the planar ultrasonic detector on the flexible substrate does not overlap with an orthographic projection of the supporting structure on the flexible substrate. That is, no supporting structure is disposed on the side of the planar ultrasonic detector proximate to the flexible substrate.

By providing the different types of ultrasonic detectors in the flexible sensor, depending on actual requirements, which type of ultrasonic detectors emits the ultrasonic waves may be controlled. For example, the actual requirement is coarse measurement, and then only the planar ultrasonic detectors may be controlled to emit the ultrasonic waves. For another example, the actual requirement is accurate measurement, and then the recessed ultrasonic detectors may be controlled to emit the ultrasonic waves. For another example, the actual requirement is small-dosage ultrasonic repairing, and then the raised ultrasonic detectors may be controlled to emit the ultrasonic waves. For another example, the actual requirement is large-dosage ultrasonic repairing, and then the recessed ultrasonic detectors may be controlled to emit the ultrasonic waves.

Figure 13:
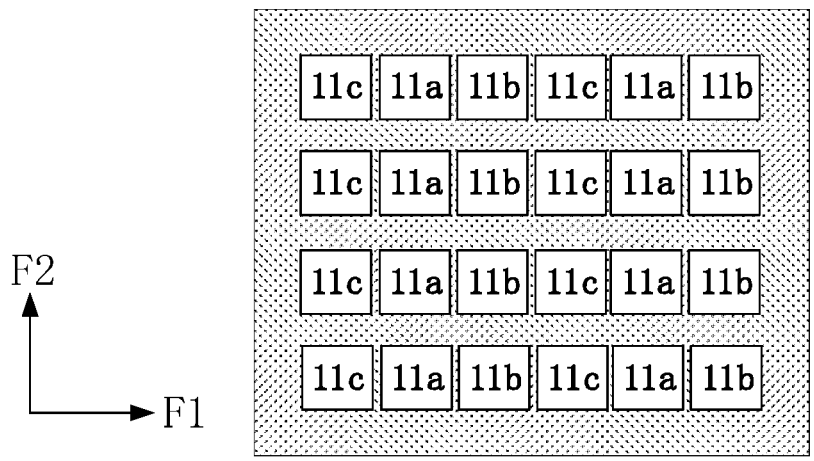
FIG. 13 is a second schematic diagram of a planar structure of a flexible sensor according to an embodiment of the present disclosure.

In an implementation, in the flexible sensor provided by the embodiments of the present disclosure, as shown in FIG. 13, the plurality of ultrasonic detectors (as shown by 11a, 11b and 11c in the figure) are arranged in an array in a first direction F1 and a second direction F2; and the first direction F1 and the second direction F2 mutually intersect.

The raised ultrasonic detectors 11a, the recessed ultrasonic detectors 11b and the planar ultrasonic detectors 11c are periodically arranged in a set sequence in the first direction F1. As shown in FIG. 13, in the first direction F1, the planar ultrasonic detectors 11c, the raised ultrasonic detectors 11a and the recessed ultrasonic detectors 11b are periodically arranged in a circulating manner.

A row of ultrasonic detectors in the second direction F2 is the same in type. As shown in FIG. 13, in the second direction F2, the first row is all planar ultrasonic detectors 11c, the second row is all raised ultrasonic detectors 11a, and the third row is all recessed ultrasonic detectors 11b.

With this arrangement, the distribution of the ultrasonic detectors of each type can be relatively uniform, resulting in good uniformity of the ultrasonic waves emitted by the plurality of ultrasonic detectors of each type. It should be noted that FIG. 13 only shows one arrangement, is illustrated by way of example with a limited number of ultrasonic detectors and does not limit the number and arrangement of the ultrasonic detectors.

During specific implementation, in the flexible sensor provided by the embodiments of the present disclosure, as shown in FIG. 13, the ultrasonic detectors may be consistent in shape and identical in area. In this way, for the same type of ultrasonic detectors, in the case of applying the same voltage, the ultrasonic waves emitted by the ultrasonic detectors have the approximately same intensity, so that the ultrasonic waves emitted by the ultrasonic detectors have good uniformity.

Figure 14:
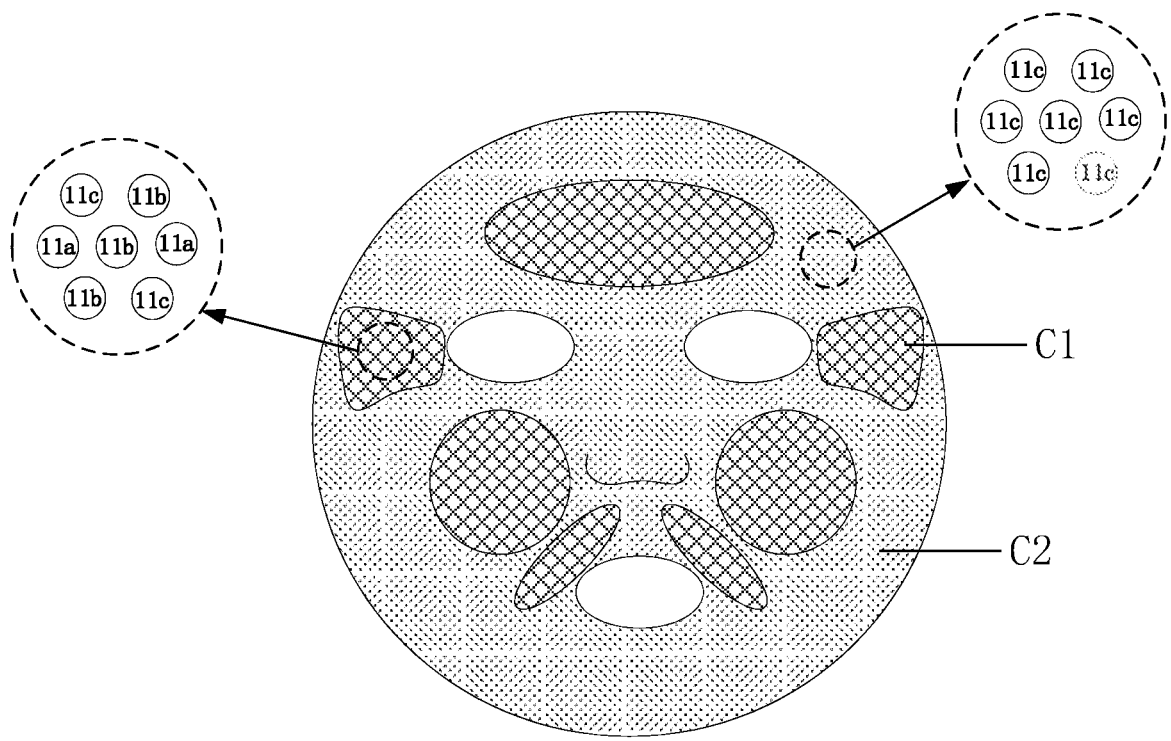
FIG. 14 is a third schematic diagram of a planar structure of a flexible sensor according to an embodiment of the present disclosure.

Optionally, in the flexible sensor provided by the embodiments of the present disclosure, as shown in FIG. 14, a detection region of the flexible sensor includes: at least one first detection region C1, and a second detection region C2 in addition to the first detection region C1.

The raised ultrasonic detectors 11a, the recessed ultrasonic detectors 11b and the planar ultrasonic detectors 11c are provided in the first detection region C1.

Only the planar ultrasonic detectors 11c are disposed in the second detection region C2.

In the practical application, depending on actual requirements, which detection region emits the ultrasonic waves may be controlled, so that multiple detection or skin repairing requirements can be met. For example, the actual requirement is accurate measurement, and then the ultrasonic detectors in each first detection region C1 may be controlled to emit the ultrasonic waves. For another example, the actual requirement is coarse measurement, and then the ultrasonic detectors in the second direction region C2 may be controlled to emit the ultrasonic waves. For another example, when the actual requirement is skin repairing, the ultrasonic detectors in each first detection region C1 may also be controlled to emit the ultrasonic waves.

Figure 15:
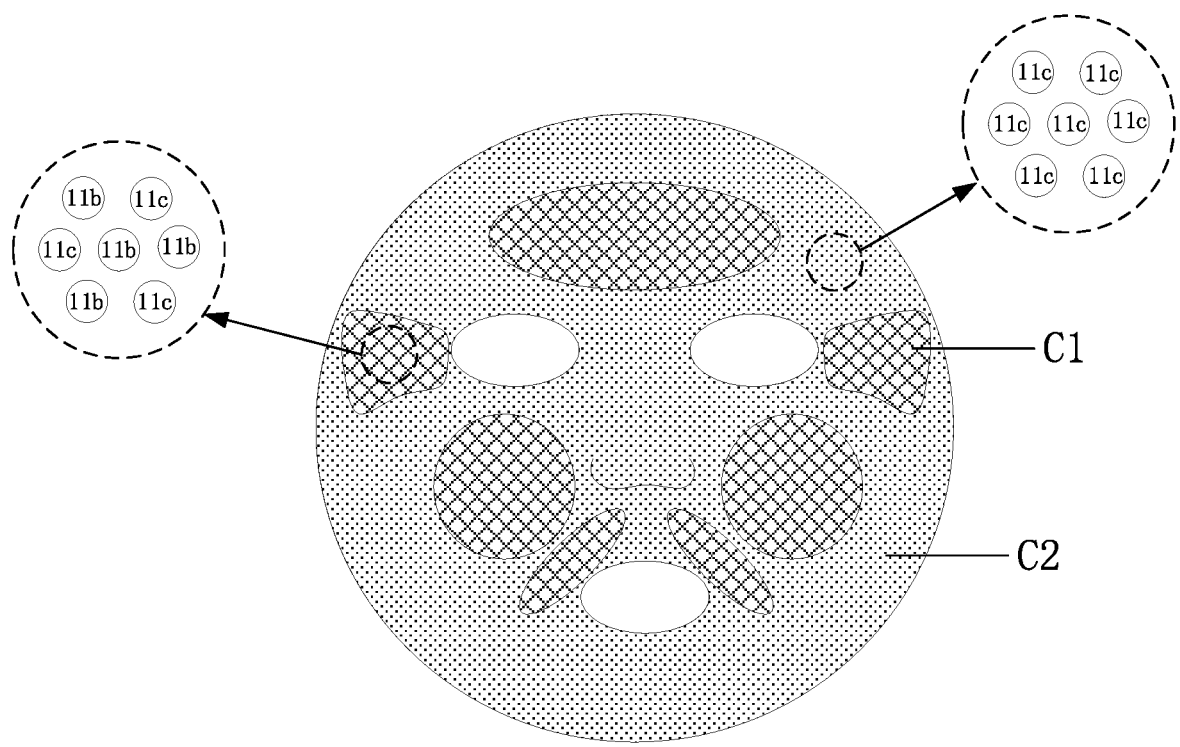
FIG. 15 is a fourth schematic diagram of a planar structure of a flexible sensor according to an embodiment of the present disclosure.

During specific implementation, in the flexible sensor provided by the embodiments of the present disclosure, as shown in FIG. 15, a detection region of the flexible sensor includes: at least one first detection region C1, and a second detection region C2 in addition to the first detection regions C1.

The recessed ultrasonic detectors 11b and the planar ultrasonic detectors 11c are disposed in the first detection regions C1.

Only the planar ultrasonic detectors 11c are disposed in the second detection region C2.

The recessed structures are disposed on sides of the recessed ultrasonic detectors 11b proximate to the flexible substrate.

An orthographic projection of the planar ultrasonic detectors 11c on the flexible substrate does not overlap with an orthographic projection of the supporting structures on the flexible substrate.

In the practical application, depending on actual requirements, which detection region emits the ultrasonic waves may be controlled, so that multiple detection or skin repairing requirements can be met. For example, the actual requirement is accurate measurement, and then the ultrasonic detectors in each first detection region C1 may be controlled to emit the ultrasonic waves. For another example, the actual requirement is coarse measurement, and then the ultrasonic detectors in the second direction region C2 may be controlled to emit the ultrasonic waves. For another example, when the actual requirement is skin repairing, the ultrasonic detectors in each first detection region C1 may also be controlled to emit the ultrasonic waves.

During specific implementation, except the structures shown in FIG. 14 and FIG. 15, the type of the ultrasonic detectors in the first detection region C1 may also be set according to actual requirements. For example, only the raised ultrasonic detectors may be disposed in the first detection region C1, or only the recessed ultrasonic detectors may be disposed in the first detection region C1, and the type of the ultrasonic detectors in the first detection region C1 is not limited here. Moreover, in FIG. 14 and FIG. 15, taking a flexible sensor for face detection as an example, the shape of the flexible sensor is consistent with the shape of the face. During specific implementation, the shape of the flexible sensor may be set according to portions which actually need to be detected, which is not limited here.

Figure 16:
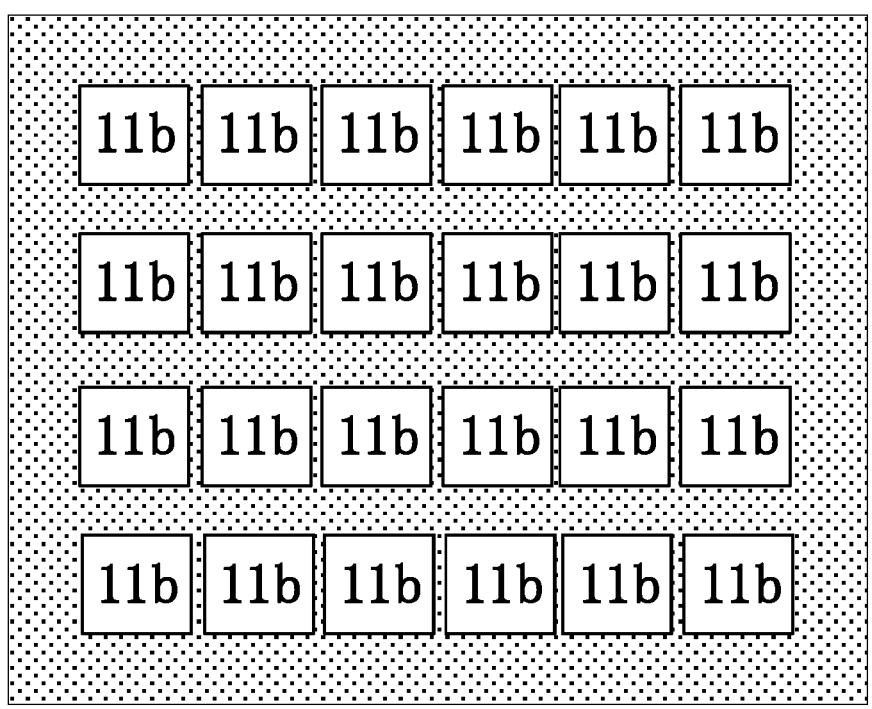
FIG. 16 is a fifth schematic diagram of a planar structure of a flexible sensor according to an embodiment of the present disclosure.

Optionally, in the flexible sensor provided by the embodiments of the present disclosure, as shown in FIG. 16, only the recessed ultrasonic detectors 11b are disposed in a detection region of the flexible sensor.

The recessed structures are disposed on sides of the recessed ultrasonic detectors 11b proximate to the flexible substrate.

A width of the recessed structures is in a range between 2 mm and 6 mm.

A depth of grooves of the recessed structures is in a range between 0.5 mm and 1.5 mm.

By providing the recessed structures with the large width and the deep grooves, the focusing depth of the recessed ultrasonic detectors 11b may be made large, so that the flexible detection device may be used for skin repairing. During specific implementation, the shape of the flexible sensor may be set according to the shape of a portion where skin repairing is actually required. For example, when forehead repairing is required, the flexible sensor may be set in an elongated strip, and the shape of the flexible sensor is not limited here.

In the practical application, the detection depth of the recessed ultrasonic detector may be on the upper and lower portions or the upper, middle and lower portions of the dermis by setting the size of the recessed structure, and the detection depths corresponding to the recessed structures of different sizes are exemplified below with reference to the figures.

Figure 17:
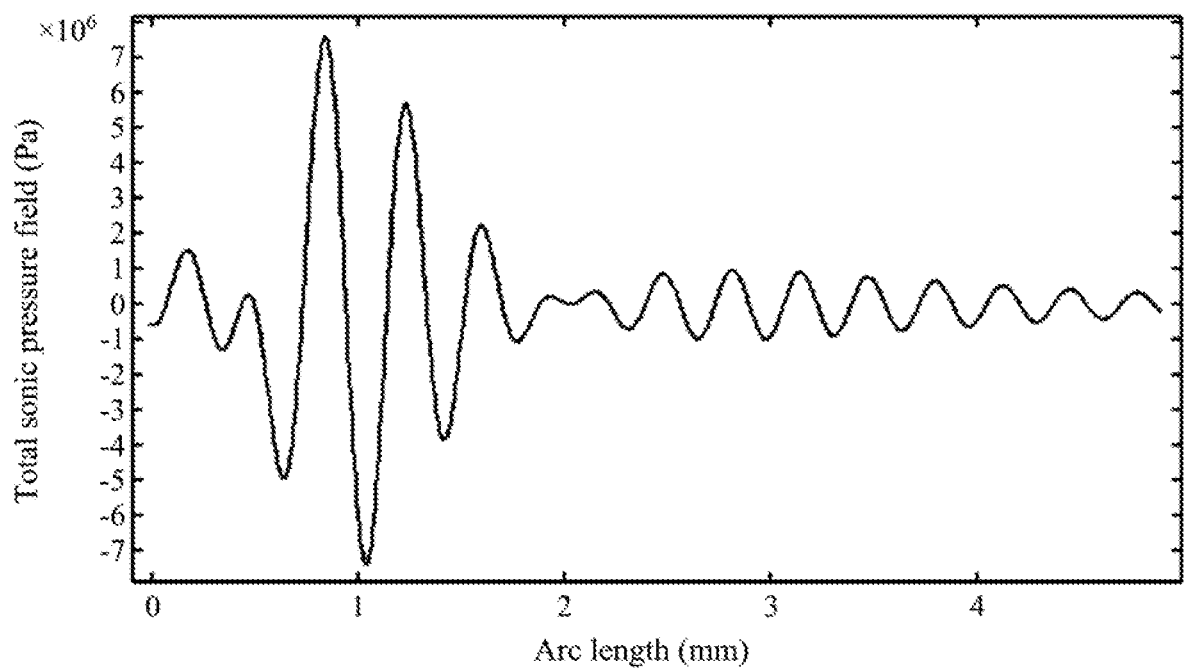
FIG. 17 is a schematic diagram of change of a total acoustic field with a detection depth of a recessed ultrasonic detector when a groove of a recessed structure has a depth of 0.75 mm and a width of the recessed structure is 3 mm.

FIG. 17 is a schematic diagram of change of a total acoustic field with a detection depth of a recessed ultrasonic detector when a groove of the recessed structure has a depth of 0.75 mm and a width of the recessed structure is 3 mm. In the figure, the abscissa (arc length) represents the detection depth, and the ordinate represents a total sonic pressure field of the ultrasonic wave emitted by the ultrasonic detector. As shown in FIG. 17, the total sonic pressure field intensity of the ultrasonic wave emitted by the recessed ultrasonic detector reaches 7e6 Pa which is nearly 10 times an initial value, that is, the focusing energy of the ultrasonic wave emitted by the recessed ultrasonic detector is high, and the focusing depth is in a range between 0.8 mm and 1.2 mm, that is, the focusing depth of the ultrasonic wave emitted by the recessed ultrasonic detector is also large.

Figure 18:
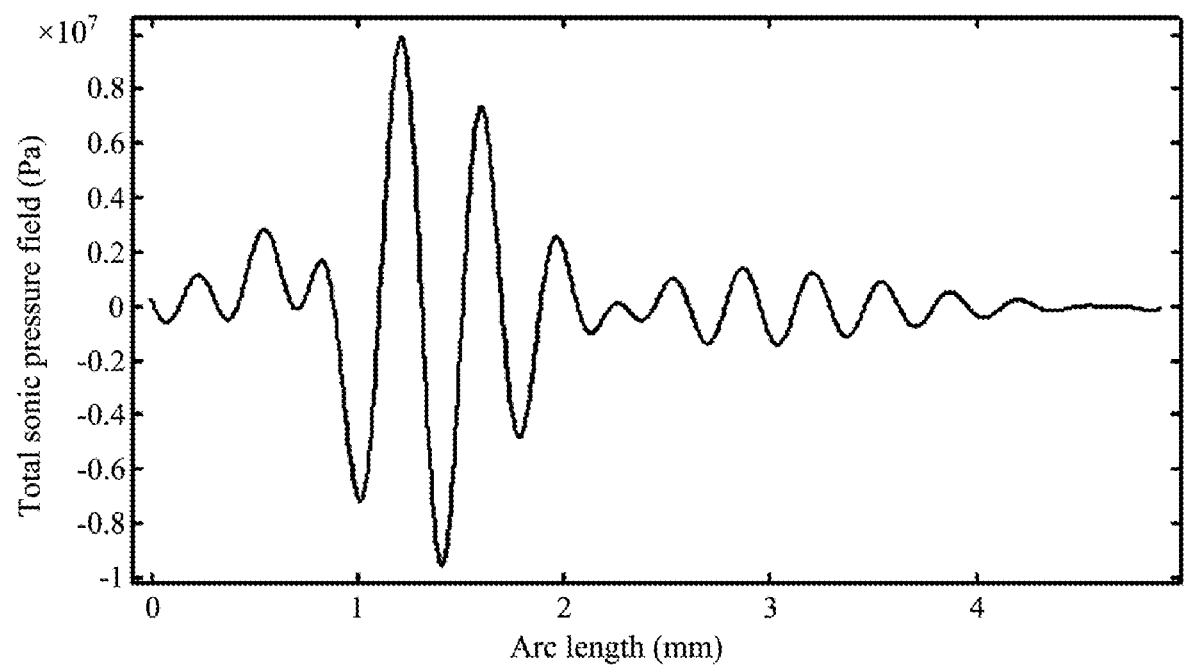
FIG. 18 is a schematic diagram of change of a total acoustic field with a detection depth of a recessed ultrasonic detector when a groove of a recessed structure has a depth of 1 mm and a width of the recessed structure is 4 mm.

FIG. 18 is a schematic diagram of change of a total acoustic field with a detection depth of a recessed ultrasonic detector when a groove of a recessed structure has a depth of 1 mm and a width of the recessed structure is 4 mm. In the figure, the abscissa (arc length) represents the detection depth, and the ordinate represents a total sonic pressure field of the ultrasonic wave emitted by the ultrasonic detector. As shown in FIG. 18, the focusing depth of the ultrasonic wave emitted by the recessed ultrasonic detector is in a range between 1.2 mm and 1.6 mm. It can be known by comparing FIG. 17 and FIG. 18 that the focusing depth and intensity of the ultrasonic wave emitted by the recessed ultrasonic detector are both increased after the width of the recessed structure and the depth of the groove are increased.

Figure 19:
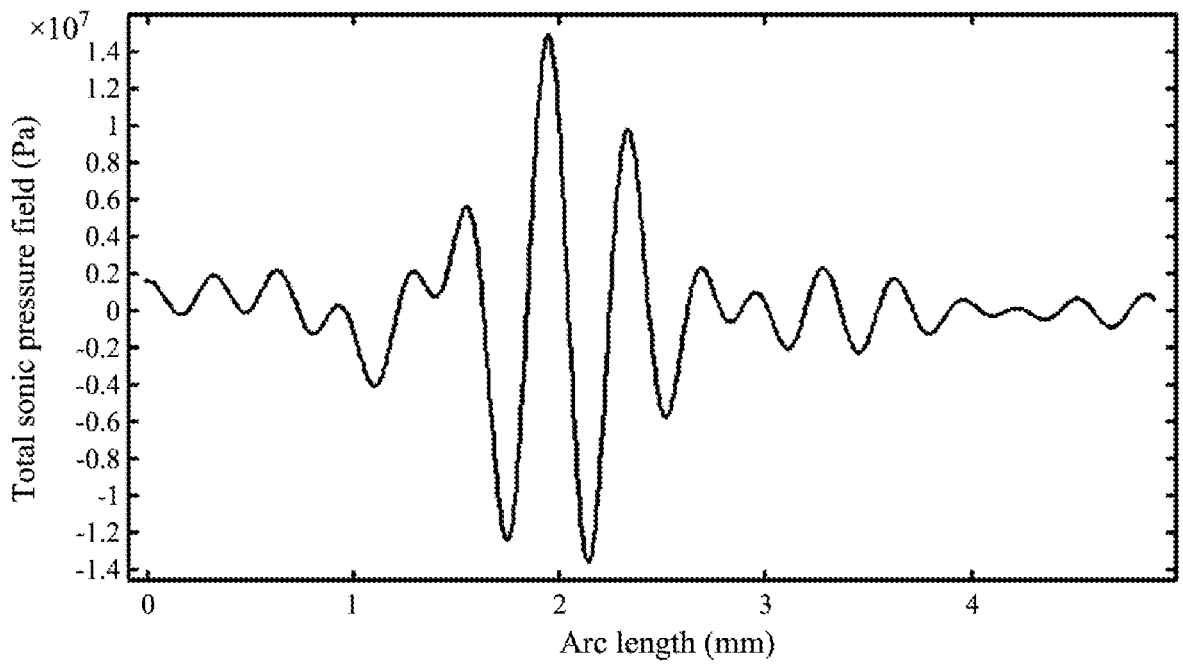
FIG. 19 is a schematic diagram of change of a total acoustic field with a detection depth of a recessed ultrasonic detector when a groove of a recessed structure has a depth of 1.5 mm and a width of the recessed structure is 6 mm.

FIG. 19 is a schematic diagram of change of a total acoustic field with a detection depth of a recessed ultrasonic detector when a groove of the recessed structure has a depth of 1.5 mm and a width of the recessed structure is 6 mm. In the figure, the abscissa (arc length) represents the detection depth, and the ordinate represents a total sonic pressure field of ultrasonic wave emitted by the ultrasonic detector. As shown in FIG. 19, the focusing depth of the ultrasonic wave emitted by the recessed ultrasonic detector is about 2 mm, and the detection depth can reach the bottom layer of the dermis.

Specifically, where the width of the recessed structure does not vary, the smaller the depth of the groove of the recessed structure, the greater the focusing depth of the ultrasonic wave emitted by the recessed ultrasonic detector, and thus the size of the recessed structure may be set according to the actual desired detection depth in addition to the sizes shown in FIGS. 17, 18 and 19, and the sizes of the recessed structure are not limited here.

During specific implementation, in order to make the focusing effect of the recessed ultrasonic detector good, the size of the recessed structure needs to be set to be large, resulting in lowered detection accuracy of the flexible sensor. Based thereon, in the flexible sensor provided by the embodiments of the present disclosure, by providing raised structures distributed around the recessed structure, i.e. by providing the raised ultrasonic detectors around the recessed ultrasonic detector, the raised ultrasonic detectors emit diverged ultrasonic waves, which may improve the uniformity of the ultrasonic wave emitted by the flexible sensor, and thus the detection accuracy of the flexible sensor is enhanced.

Figure 20:
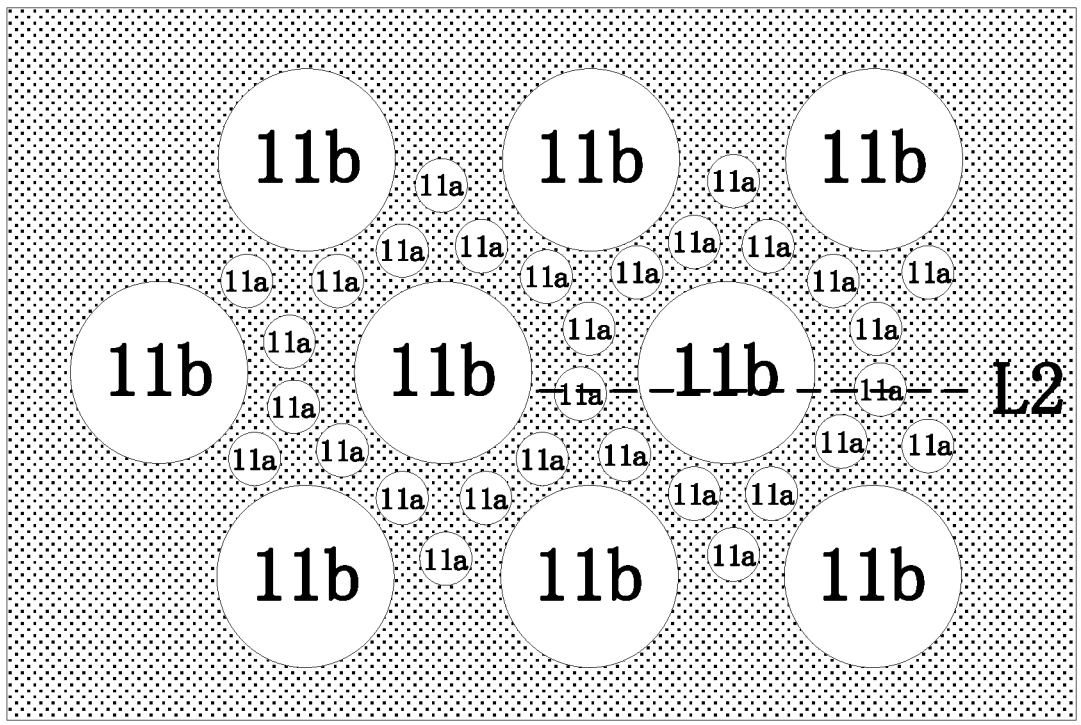
FIG. 20 is a schematic diagram of a planar structure of a flexible sensor according to an embodiment of the present disclosure.
Figure 21:
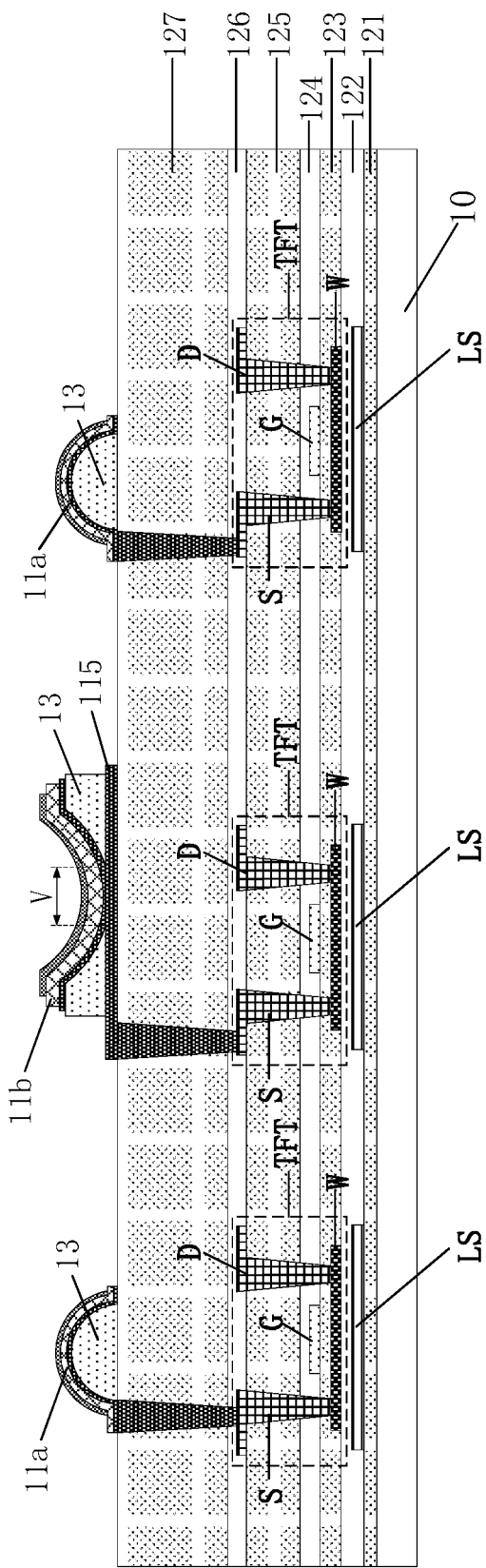
FIG. 21 is a schematic cross-sectional diagram at a dashed line L2 in FIG. 20.

Specifically, FIG. 20 is a schematic diagram of a planar structure of the flexible sensor according to the embodiments of the present disclosure. FIG. 21 is a schematic cross-sectional diagram at the dashed line L2 in FIG. 20. As shown in FIG. 20 and FIG. 21, the plurality of recessed ultrasonic detectors 11b and the raised ultrasonic detectors 11a distributed around the recessed ultrasonic detectors 11b are disposed in a detection region of the flexible sensor.

The raised structures are disposed on sides of the raised ultrasonic detectors 11a proximate to the flexible substrate 10.

The recessed structures are disposed on sides of the recessed ultrasonic detectors 11b proximate to the flexible substrate 10.

FIG. 20 only takes one arrangement as an example for illustration, during specific implementation, the number and arrangement of the raised ultrasonic detectors 11a may be set according to spaces between the adjacent recessed ultrasonic detectors 11b, which is not limited here.

In the practical application, the ultrasonic detectors may be controlled to emit the ultrasonic waves according to actual requirements. For example, when accurate detection or large-dosage focusing skin repairing is needed, the recessed ultrasonic detectors 11b may be controlled to emit the ultrasonic waves. For another example, when small-dosage ultrasonic skin repairing or coarse detection is needed, the raised ultrasonic detectors 11a may be controlled to emit the ultrasonic waves so as to make the ultrasonic wave emitted by the flexible sensor uniform. For another example, when accurate detection is needed, the raised ultrasonic detectors 11a and the recessed ultrasonic detectors 11b may be controlled to both emit the ultrasonic waves, so that the detection accuracy of the flexible sensor is improved.

In the flexible sensor shown in FIG. 20, the size of the recessed structure may be greater than that of the raised structure, specifically, the width of the recessed structure may be set in a range between 1 mm and 3 mm, for example, the width may be set in a range between 1 mm and 2 mm, and the depth of the groove of the recessed structure may be set in a range between 0.15 mm and 0.75 mm, for example, the depth may be set in a range between 0.15 mm and 0.5 mm. The width of the raised structure may be set in a range between 50 μm and 200 μm, for example, the width may be set in a range between 50 μm and 100 μm. The maximum height of the raised structure may be set in a range between 15 μm and 80 μm, for example, the maximum height may be set in a range between 15 μm and 50 μm. Moreover, the spacing between the adjacent raised structure may be set in a range between 50 μm and 500 μm and may be obtained by calculation according to the positions of the recessed structures, for example, the spacing between the adjacent raised structures may be set in a range between 100 μm and 300 μm.

In the practical application, when the recessed structure and the raised structure in the flexible sensor are different in size, the ultrasonic waves emitted by the flexible sensor have different uniformity. Analysis is performed below in conjunction with a simulation experiment. Example one, the width of the recessed structures is 1 mm, the depth of the grooves is 250 μm, the width of the raised structures is 100 μm, the maximum height of the raised structures is 25 μm, the spacing between the adjacent recessed structures is 200 μm, and the spacing between the adjacent raised structures is 71.2 μm. Example two, the width of the recessed structures is 1 mm, the depth of the grooves is 250 μm, the width of the raised structures is 200 μm, the maximum height of the raised structures is 50 μm, the spacing between the adjacent recessed structures is 200 μm, and the spacing between the adjacent raised structures is 21.2 μm. Example three, the width of the recessed structures is 2 mm, the depth of the grooves is 500 μm, the width of the raised structures is 100 μm, the maximum height of the raised structures is 25 μm, the spacing between the adjacent recessed structures is 200 μm, and the spacing between the adjacent raised structures is 38.8 μm. Simulated analysis is performed on example one, example two and example three respectively to obtain: in contrast to example one, the uniformity of the ultrasonic waves emitted by the flexible sensors in examples two and three is good, it can be known by comparing example one and example two that by increasing the size of the raised structure, the uniformity of the ultrasonic wave emitted by the flexible sensor can be increased; and it can be known by comparing example one and example three that by increasing the size of the recessed structure, the uniformity of the ultrasonic wave emitted by the flexible sensor can also be increased. The sizes of the raised structure and the recessed structure are only exemplified herein for analysis, and during specific implementation, the sizes of the raised structure and the recessed structure may be set according to actual needs, which is not limited here.

In addition, the flexible sensor provided by the embodiments of the present disclosure may further be combined with an optical sensor detection device, a display device and other devices so as to achieve more functions.

According to the flexible sensor provided by the embodiments of the present disclosure, by providing the plurality of ultrasonic detectors on the flexible substrate, the flexible sensor can be bent, so that the flexible sensor can be attached to the skin for detection. Besides, by providing the plurality of ultrasonic detectors on the flexible substrate, the detection area of the flexible sensor is large. In addition, by forming the plurality of holes in the region other than the region where the detection circuits are located, stress can be released, and the performance of the ultrasonic detectors is prevented from being affected when the flexible sensor is bent. Moreover, by providing the different types of ultrasonic detection devices, the flexible sensor can achieve various functions, so that user experience is improved.

While the preferred embodiments of the present disclosure have been described, further variations and modifications of these embodiments may be made by those skilled in the art once the basic inventive concepts have come to mind. It is therefore intended that the appended claims be construed to include the preferred embodiments along with all changes and modifications that fall within the scope of the disclosure.

It will be apparent to those skilled in the art that various modifications and variations can be made to the embodiments of the present disclosure without departing from the spirit and scope of the embodiments of the present disclosure. Thus, it is intended that the present disclosure include such modifications and variations of the embodiments of the present disclosure provided they come within the scope of the claims of the present disclosure and their equivalents.

What is claimed is:

1. A flexible sensor, comprising:
   a flexible substrate;
   a plurality of ultrasonic detectors on stacked film layers on the flexible substrate; and
   a plurality of detection circuits in the stacked film layers, respectively corresponding to the plurality of ultrasonic detectors;
   wherein:
   each detection circuit of the plurality of detection circuits is between the flexible substrate and an ultrasonic detector of the plurality of ultrasonic detectors, and configured to drive the ultrasonic detector of the plurality of ultrasonic detectors to emit ultrasonic waves, and detect a detection signal output by the ultrasonic detector after the ultrasonic detector receives the ultrasonic waves; and the ultrasonic detector of the plurality of ultrasonic detectors corresponds to a detection circuit of the plurality of detection circuits;
   the plurality of ultrasonic detectors comprises: a plurality of raised ultrasonic detectors and at least one recessed ultrasonic detector; wherein,
   each of the plurality of raised ultrasonic detectors comprises:
   a first supporting structure located on the flexible substrate and protruding along a direction pointing from the flexible substrate to the plurality of ultrasonic detectors, wherein the first supporting structure is a raised structure;
   a first electrode located on a side of the first supporting structure away from the flexible substrate and coupled to one detection circuit of the plurality of detection circuits;
   a second electrode on a side of the first electrode away from the flexible substrate; and
   a piezoelectric induction layer between the first electrode and the second electrode; and
   each of the at least one recessed ultrasonic detector comprises:

a second supporting structure located on the flexible substrate and concaved along the direction pointing from the flexible substrate to the plurality of ultrasonic detectors, wherein the second supporting structure is a recessed structure having a groove on a side away from the flexible substrate;

a first electrode located on a side of the second supporting structure away from the flexible substrate and coupled to another detection circuit of the plurality of detection circuits;

a second electrode on a side of the first electrode away from the flexible substrate; and a piezoelectric induction layer between the first electrode and the second electrode;

the plurality of raised ultrasonic detectors surrounds each of the at least one recessed ultrasonic detector;

a size of an orthographic projection of each of the plurality of raised ultrasonic detectors on the flexible substrate is smaller than a size of an orthographic projection of each of the at least one recessed ultrasonic detector on the flexible substrate; and a plurality of holes extend through at least a part of the stacked film layers, and an orthographic projection of the plurality of detection circuits on the flexible substrate is not overlapped with an orthographic projection of the plurality of holes on the flexible substrate.

2. The flexible sensor according to claim 1, wherein each of the plurality of raised ultrasonic detectors extends along a first surface of the first supporting structure, and the first surface is a surface of the first supporting structure away from the flexible substrate; and each of the at least one recessed ultrasonic detector extends along a first surface of the second supporting structure, and the first surface is a surface of the second supporting structure away from the flexible substrate.

3. The flexible sensor according to claim 1, wherein: a width of the raised structure is in a range between 50 μm and 500 μm;

a spacing between the raised structure and another raised structure that is adjacent to the raised structure is in a range between 100 μm and 300 μm;

a value of the spacing between the raised structure and the another raised structure adjacent to the raised structure is not equal to a value of the width of the raised structure; and a maximum height of the raised structure is in a range between 15 μm and 80 μm.

4. The flexible sensor according to claim 1, wherein an opening is formed in the groove of the recessed structure;

the flexible sensor further comprises: a conductive connection portion between the another detection circuit and the recessed structure; and the conductive connection portion is coupled to the first electrode through the opening, and the conductive connection portion is coupled to the another detection circuit.

5. The flexible sensor according to claim 1, wherein:
a width of the recessed structure is in a range between 1 mm and 3 mm; and a depth of the groove of the recessed structure is in a range between 0.15 mm and 0.75 mm.

6. The flexible sensor according to claim 5, wherein:
the width of the recessed structure is in a range between 1 mm and 2 mm; and the depth of the groove of the recessed structure is in a range between 0.15 mm and 0.5 mm.

7. The flexible sensor according to claim 1, wherein the plurality of ultrasonic detectors further comprises at least one planar ultrasonic detector having a planer structure;

an orthographic projection of the at least one planar ultrasonic detector on the flexible substrate does not overlap with an orthographic projection of the first and second supporting structures on the flexible substrate.

8. The flexible sensor according to claim 7, wherein a detection region of the flexible sensor comprises: at least one first detection region, and a second detection region in addition to the first detection region;

the plurality of raised ultrasonic detector, the at least one recessed ultrasonic detector and the at least one planar ultrasonic detector are in the first detection region; and only another at least one planar ultrasonic detector is in the second detection region.

9. The flexible sensor according to claim 1, wherein a detection region of the flexible sensor comprises: at least one first detection region, and a second detection region in addition to the first detection region;

the at least one recessed ultrasonic detector and the at least one planar ultrasonic detector are in the first detection region;

only another at least one planar ultrasonic detector is in the second detection region;

the recessed structure is on the side of the at least one recessed ultrasonic detector proximate to the flexible substrate; and an orthographic projection of the at least one planar ultrasonic detector on the flexible substrate does not overlap with an orthographic projection of the first and second supporting structures on the flexible substrate.

10. The flexible sensor according to claim 1, wherein only the at least one recessed ultrasonic detector is in a detection region of the flexible sensor;

the recessed structure is on the side of the at least one recessed ultrasonic detector proximate to the flexible substrate;

a width of the recessed structure is in a range between 2 mm and 6 mm; and a depth of the groove of the recessed structure is in a range between 0.5 mm and 1.5 mm.

11. The flexible sensor according to claim 1, wherein each of the plurality of detection circuits comprises a thin film transistor comprising a gate, a source, a drain, a passivation layer and a flat layer.

12. The flexible sensor according to claim 11, the first electrode is coupled to the source through a via extending through the passivation layer and the flat layer.

13. The flexible sensor according to claim 12, wherein a position of the raised structure or the recessed structure is set by avoiding a position where the via is located.

\* \* \* \* \*